(12) United States Patent
Davis

(10) Patent No.: US 12,398,428 B2
(45) Date of Patent: Aug. 26, 2025

(54) DARC EXPRESSION AS PROGNOSTICATOR OF IMMUNOTHERAPY OUTCOMES

(71) Applicant: Cornell University, Ithaca, NY (US)

(72) Inventor: Melissa B. Davis, New York, NY (US)

(73) Assignee: Cornell University, Ithaca, NY (US)

( * ) Notice: Subject to any disclaimer, the term of this patent is extended or adjusted under 35 U.S.C. 154(b) by 1035 days.

(21) Appl. No.: 17/428,219

(22) PCT Filed: Feb. 6, 2020

(86) PCT No.: PCT/US2020/017055
§ 371 (c)(1),
(2) Date: Aug. 3, 2021

(87) PCT Pub. No.: WO2020/163628
PCT Pub. Date: Aug. 13, 2020

(65) Prior Publication Data
US 2022/0119891 A1    Apr. 21, 2022

Related U.S. Application Data

(60) Provisional application No. 62/802,135, filed on Feb. 6, 2019.

(51) Int. Cl.
| C12Q 1/6886 | (2018.01) |
| A61K 40/11 | (2025.01) |
| A61K 40/31 | (2025.01) |
| A61K 40/42 | (2025.01) |
| C07K 16/28 | (2006.01) |

(52) U.S. Cl.
CPC ............ *C12Q 1/6886* (2013.01); *A61K 40/11* (2025.01); *A61K 40/31* (2025.01); *A61K 40/42* (2025.01); *C07K 16/2818* (2013.01); *C07K 16/2827* (2013.01); *A61K 2239/49* (2023.05); *C12Q 2600/158* (2013.01)

(58) Field of Classification Search
CPC .................................................. C12Q 1/6886
See application file for complete search history.

(56) References Cited

U.S. PATENT DOCUMENTS

| 2015/0202291 | A1 | 7/2015 | Bosch et al. |
| 2018/0046771 | A1* | 2/2018 | Assefa ................... G16H 50/20 |
| 2019/0002912 | A1* | 1/2019 | Lu ............................ A61P 35/00 |
| 2020/0224282 | A1* | 7/2020 | Pietenpol ............. C12Q 1/6886 |
| 2022/0091121 | A1* | 3/2022 | Nakshatri ................ C12Q 1/68 |

OTHER PUBLICATIONS

Wang et al. Oncogene. 2006. 25:7201-7211. (Year: 2006).*
Voutsakakis. Anticancer Research. 2016. 36:5607-5622. (Year: 2016).*
Horuk, R., The Duffy Antigen Receptor for Chemokines DARC/ACKR1, Frontiers in Immunology, Jun. 5, 2015, vol. 6, 3 pages.
Horne, K., et al., Shedding light on DARC: the role of the Duffy antigen/receptor for chemokines in inflammation, Infection and malignancy, Inflammation Research, Mar. 17, 2009, vol. 58, No. 8, pp. 431-435.
Davis, M.B., et al., Distinct Transcript Isoforms of the Atypical Chemokine Receptor 1 (ACKR1) / Duffy Antigen Receptor for Chemokines (DARC) Gene Are Expressed in Lymphoblasts and Altered Isoform Levels are Associated with Genetic Ancestry and the Duffy-Null Allele, PLoS One, Oct. 16, 2015, pp. 1-16.

* cited by examiner

*Primary Examiner* — Joseph G. Dauner
(74) *Attorney, Agent, or Firm* — Hodgson Russ LLP

(57) ABSTRACT

Methods for prognosticating if an individual afflicted with a malignant tumor is likely to respond favorably to immunotherapy comprising testing for the presence or absence of DARC expression in the tumor, and if no DARC expression is detected, identifying the individual as not being suitable for immunotherapy, and optionally administering an anti-cancer therapy other than immunotherapy to the individual, or if DARC expression is detected, then identifying the individual as being suitable for immunotherapy, and optionally administering immunotherapy or any other anti-cancer therapy to the individual.

5 Claims, 26 Drawing Sheets

Specification includes a Sequence Listing.

G

A

C

D

A

B

C

C

| Comparison Groups | B cells naive | B cells memory | T cells CD8 | T cells CD4 memory resting | T cells follicular helper | T cells regulatory (Tregs) | T cells gamma delta | NK cells resting | Monocytes | Macrophages M1 | Macrophages M2 | Mast cells resting |
|---|---|---|---|---|---|---|---|---|---|---|---|---|
| DARC/ACKR1 high vs DARC/ACKR1 low | P<0.0001 | P<0.0001 | P<0.0001 | P<0.0001 | P<0.0001 | P<0.0001 | P=0.0059 | P<0.0001 | P<0.0001 | P<0.0001 | P<0.0001 | P<0.0001 |
| DARC/ACKR1 mid vs DARC/ACKR1 high | P<0.0001 | P=0.0014 | P<0.0001 | P<0.0001 | P=0.0057 | P<0.0001 | P=0.0170 | P=0.0213 | P<0.0001 | P=0.0015 | P<0.0001 | P<0.0001 |
| DARC/ACKR1 mid vs DARC/ACKR1 low | P=0.0033 | P=0.1574 | P=0.0060 | P=0.0064 | P=0.0012 | P=0.8133 | P=0.7785 | P=0.0874 | P=0.0879 | P=0.0731 | P<0.0001 | P<0.0001 |

DARC EXPRESSION AS PROGNOSTICATOR OF IMMUNOTHERAPY OUTCOMES

CROSS-REFERENCE TO RELATED APPLICATIONS

This application claims priority to U.S. Provisional Patent Application No. 62/802,135, filed on Feb. 6, 2019, the disclosure of which is incorporated herein by reference.

STATEMENT REGARDING FEDERALLY SPONSORED RESEARCH

This invention was made with government support under grant number CA210237-01A1 awarded by the National Institutes of Health. The government has certain rights in the invention.

BACKGROUND OF THE DISCLOSURE

Breast cancer disparities have been well-documented for over 50 years, indicating significant differences in rates of incidence and mortality among women of varying self-reported race and ethnicity (Jemal et al. 2006, *CA Cancer J Clin* 56 (2):106-30; Chlebowski et al. 2005, *J Natl Cancer Inst* 97 (6):439-48. doi: 10.1093/jnci/dji064). Recent studies have identified biological factors that may be associated with disparate clinical outcomes, including disproportionate burdens of aggressive tumor subtypes (i.e. triple-negative basal-like) in women of west African descent (Silber et al. 2013, *JAMA* 310 (4):389-97; Amirikia et al. 2011, *Cancer* 117 (12):2747-53; Chollet-Hinton et al. 2017, *Cancer Epidemiol Biomarkers Prev* 26 (12):1722-1729; Jiagge et al. 2016, *Ann Surg Oncol* 23 (12):3843-3849). Overall, women of African descent are more likely to be diagnosed with the worst types of breast cancer, including Triple-Negative Breast Cancer (TNBC), at earlier ages with the poorest prognosis indications (Amirikia et al. 2011, *Cancer* 117 (12):2747-53; Joslyn and West 2000, *Cancer* 88 (1):114-23; Lund et al. 2009, *Breast Cancer Res Treat* 113 (2):357-70; Clarke et al. 2012, *J Natl Cancer Inst* 104 (14):1094-101; DeSantis et al. 2014, *CA Cancer J Clin* 64 (1):52-62), despite having access to proper screening and standard treatments ((Mortel et al. 2015, *Cancer Epidemiol Biomarkers Prev* 24 (10):1599-606). As such, there is a clear need to better understand the molecular dynamics of tumor progression to facilitate appropriate treatment.

SUMMARY OF THE DISCLOSURE

Utilizing data from The Cancer Genome Atlas (TCGA), we uncovered expression pattern differences in immunological pathway genes that were associated with self-identified race and identified an enrichment in chemokine signaling. In this disclosure, we describe a key regulator of the chemokine signaling pathways, Atypical Chemokine Receptor 1 (ACKR1, aka DARC), in breast cancer case.

This disclosure is based, at least in part, on the discovery that the presence or absence of certain aberrations in the Atypical Chemokine Receptor 1 (ACKR1/DARC) gene in an individual with a malignant tumor (such as a breast tumor) are predictive of the individual's response to immunotherapy.

In an aspect, this disclosure provides a method for prognosticating if an individual afflicted with a malignant tumor will respond favorably to immunotherapy comprising testing for the presence or absence of DARC expression in the cells of the tumor, and if DARC expression is detected, then identifying the individual as being suitable for immunotherapy, but if no DARC expression is detected, identifying the individual as not being suitable for immunotherapy. If DARC expression is detected (DARC positive), then the individual may be administered any anti-cancer therapy including immunotherapy. If DARC expression is not detected (DARC negative), the individual may be administered any anti-cancer therapy except immunotherapy. Examples of immunotherapy agents include checkpoint inhibitors.

In an aspect, this disclosure provides a method for administering an anti-cancer treatment to a human patient afflicted with a malignant tumor, comprising: testing if the tumor cells are DARC negative, and if they are DARC negative, then administering to the patient a therapy that is not immunotherapy, but comprises chemotherapy, radiation therapy, antibody therapy, surgery, or any other suitable anti-cancer therapy or combinations thereof, and if the tumor cells are DARC positive, then administering immunotherapy, although other therapies (chemotherapy, radiation therapy, antibody therapy, surgery or combinations) may alternatively, or additionally be administered.

The tumor that may be subjected to prediction of treatment outcomes may be a breast, ovarian, melanoma, bladder, lung, thyroid, pancreatic, prostate, uterine, testicular, gastric, soft tissue and osteogenic sarcomas, neuroblastoma, Wilms' tumor, malignant lymphoma (Hodgkin's and non-Hodgkin's), multiple myeloma, and tumor of the head, neck, cervix, colon, or vagina, or any other malignant tumor.

BRIEF DESCRIPTION OF THE FIGURES

For a fuller understanding of the nature and objects of the disclosure, reference should be made to the following detailed description taken in conjunction with the accompanying figures.

DETAILED DESCRIPTION OF THE DISCLOSURE

Figure 1:
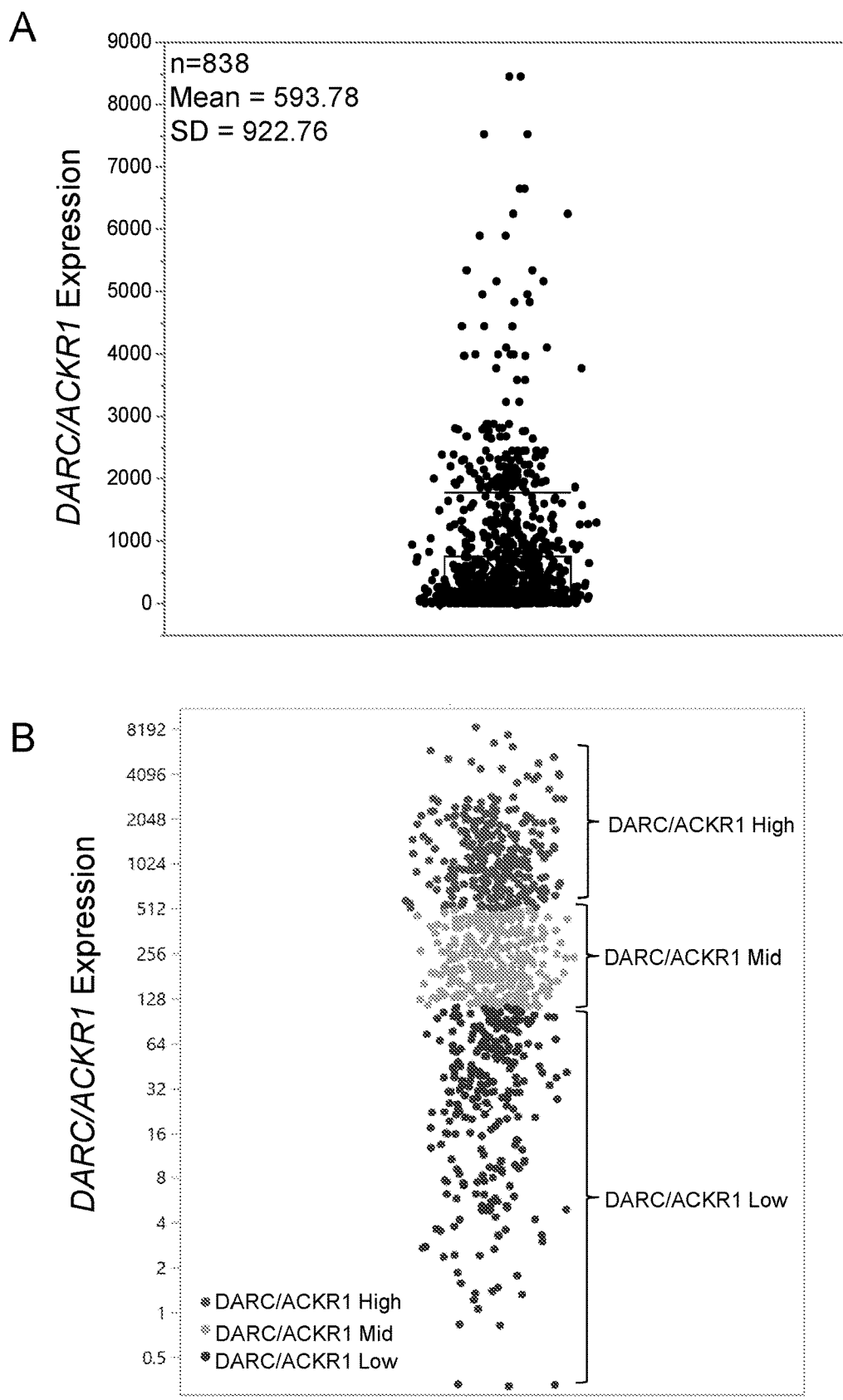
FIG. 1. DARC/ACKR1 and subtype distributions across TCGA cohort. (A) Distribution of DARC/ACKR1 gene expression across TCGA breast cancer cohort (n=838). (B) Stratification of DARC/ACKR1 gene expression broken down into high (n=289,), mid (n=268), and low (n=281) categories. (C) Distribution of DARC/ACKR1 gene expression by race (AA n=164, WA n=662). (D) DARC/ACKR1 expression across breast cancer molecular subtypes (Basal-like; HER2+; Luminal A; Luminal B). (E) Distribution of VWF gene expression categories by race (High, Mid, Low). (F) Linear regression showing positive correlation between DARC/ACKR1 and VWF mean expression (p<0.0001, $R^2$=0.517). (G) Distribution of vital status (deceased; living) among DARC/ACKR1 expression subgroups.
Figure 1:
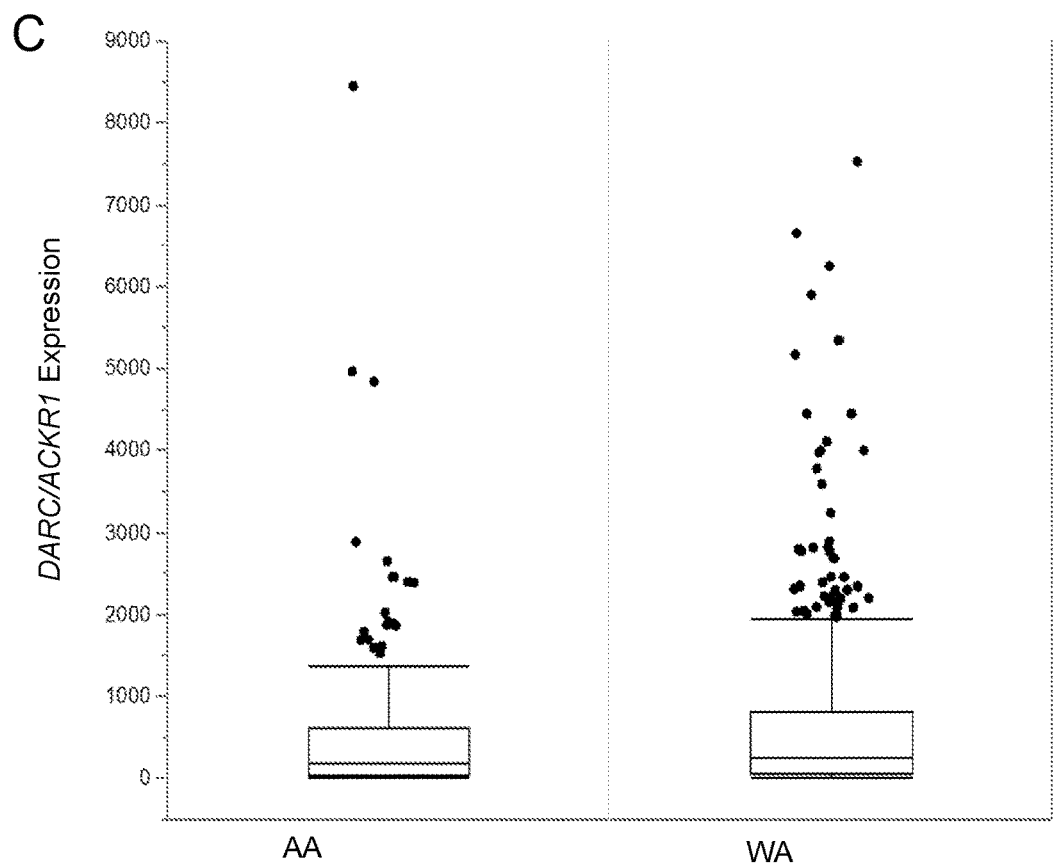
Figure 1:
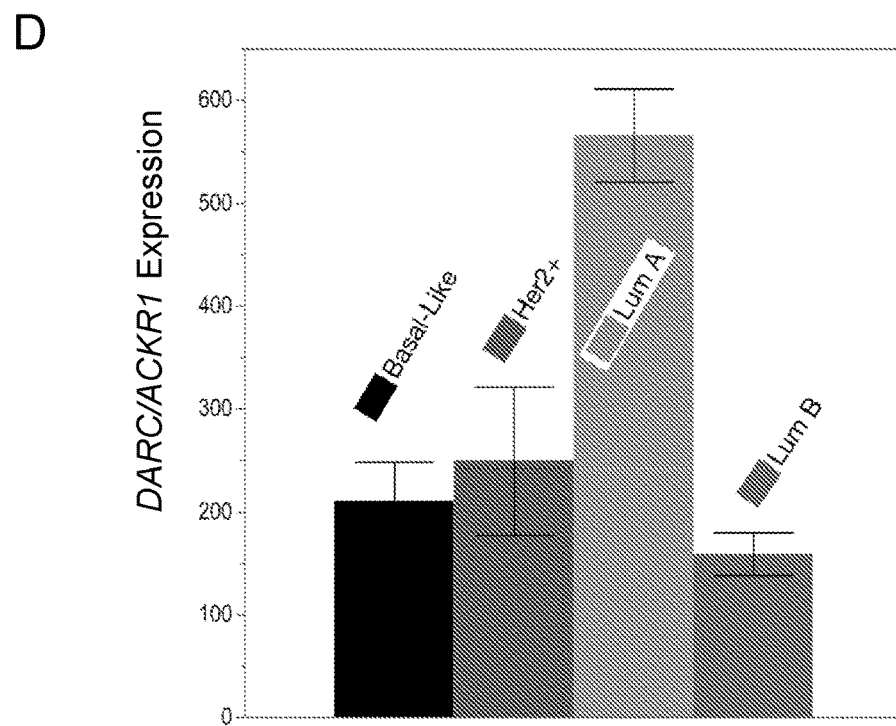
Figure 1:
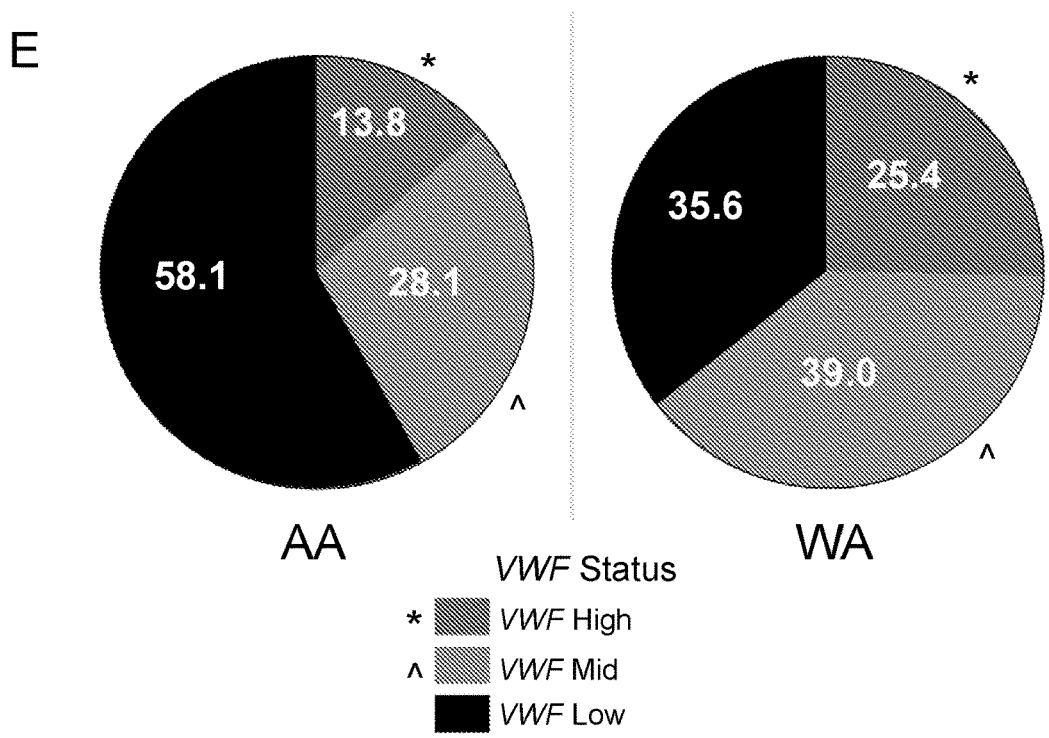
Figure 1:
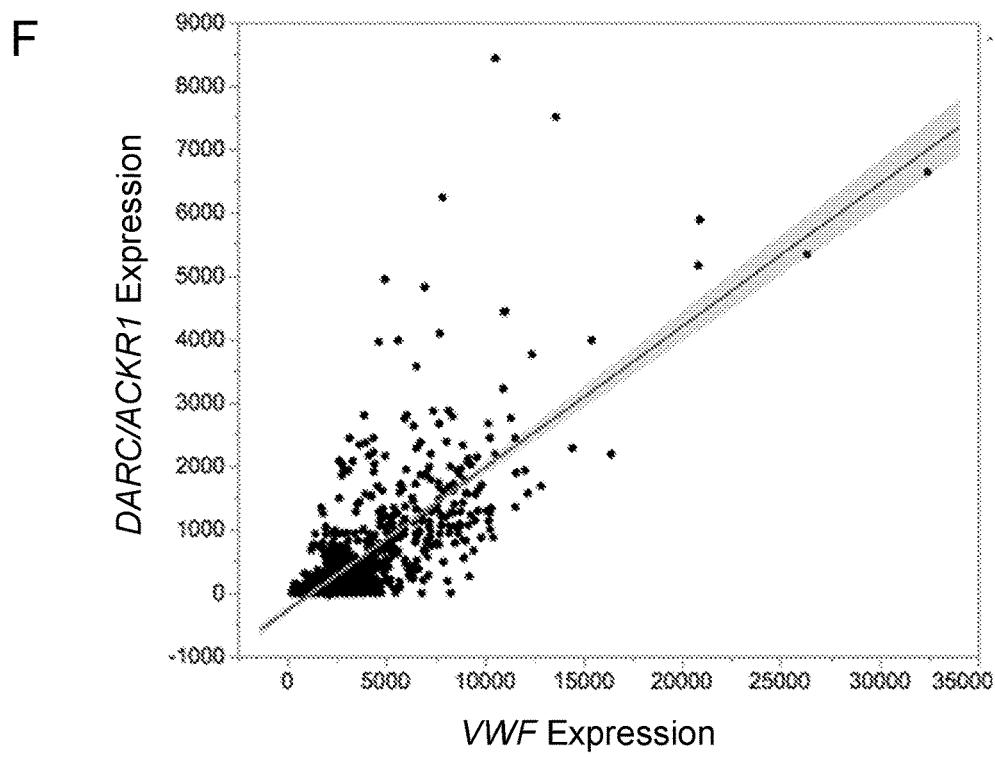
Figure 1:
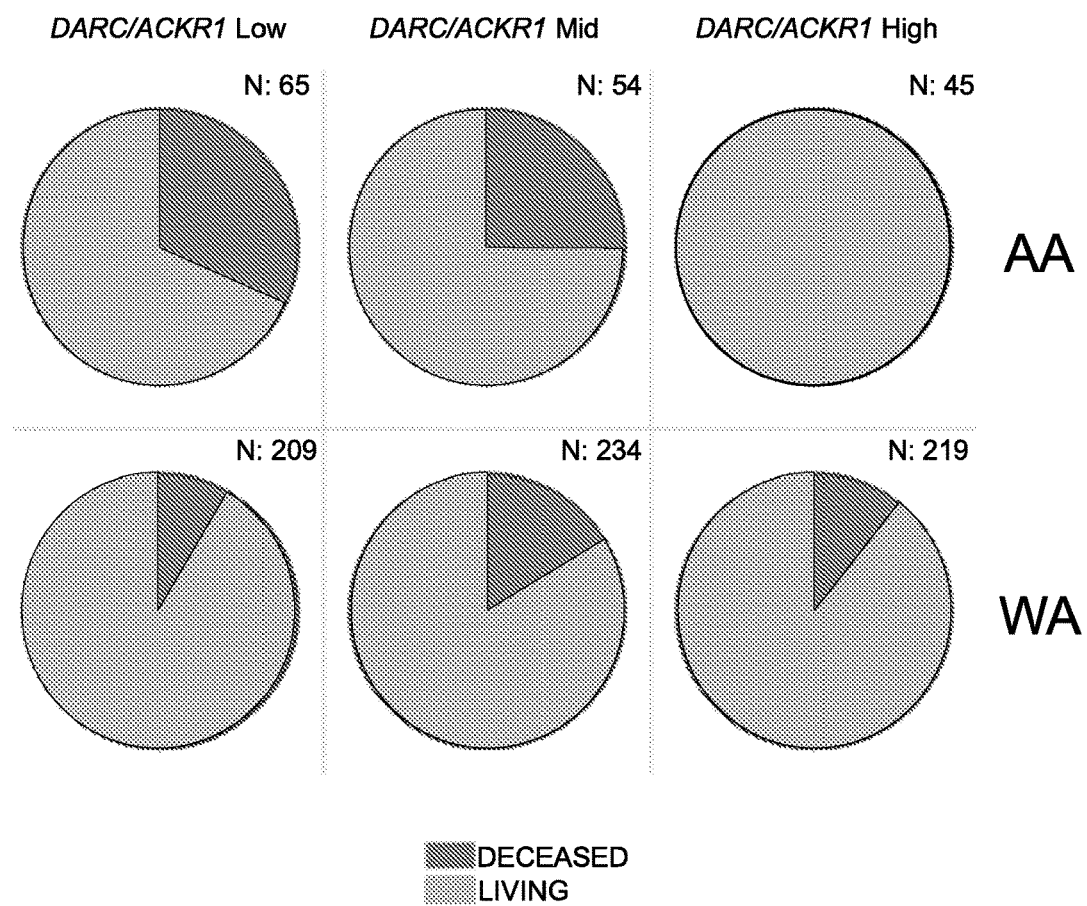

Although claimed subject matter will be described in terms of certain examples, other examples, including examples that do not provide all of the benefits and features set forth herein, are also within the scope of this disclosure. Various structural, logical, and process step changes may be made without departing from the scope of the disclosure.

Every numerical range given throughout this specification includes its upper and lower values, as well as every narrower numerical range that falls within it, as if such narrower numerical ranges were all expressly written herein.

All nucleotide sequences described herein, their RNA and DNA equivalents, and complimentary sequences are included in this disclosure. All polynucleotide and amino acid sequences associated with GenBank accession numbers (or other similar databases) described in this disclosure are incorporated herein by reference as those sequences are listed in the database as of the priority filing date of this application or patent.

The terms "a" or "an" are intended to include the singular as well as the plural of the particular item being referenced. Any reference to a singular includes its plural and vice-versa.

The term "Anti-tumor activity" is defined herein as an activity that results in any reduction in tumor mass or tumor burden after carrying out the activity, which includes administration of the compositions or methods described in the present disclosure.

A nucleotide substitution in this disclosure refers to the replacement of a nucleotide with a different nucleotide. An example of a substitution is a single nucleotide polymorphism.

A single nucleotide addition, deletion, or substitution within the genome of a person is referred to as a single nucleotide polymorphism (SNP). More specifically, a SNP may be a single base insertion or deletion variant. A SNP substitution can be considered a transition or a transversion. A transition is the replacement of one purine nucleotide by another purine nucleotide, or one pyrimidine by another pyrimidine. A transversion is the replacement of a purine by a pyrimidine, or vice versa. The standard nomenclature for representing a SNP by those skilled in the art is by a reference SNP number (rs #).

The DARC/ACKR1 is a seven-transmembrane G-protein-coupled receptor that is found on the surface of red blood cells (RBC)/erythrocytes, endothelial cells lining post-capillary venules, and most recently has been shown to be expressed on lymphoblast cells ((Davis et al. 2015, *PLoS One* 10 (10)). DARC/ACKR1 functions as a decoy receptor for a variety of CXC and CC chemokines, including those with pro-malignant and pro-inflammatory effects, such as CCL2 and CXCL8 (IL-8) (Neote et al. 1994, *Blood* 84 (1):44-52). It is considered a decoy receptor because it binds and internalizes these chemokines, and targets them for lysosomal degradation, efficiently sequestering their signaling capabilities (Peiper et al. 1995, *J Exp Med* 181 (4):1311-7; Chaudhuri et al. 1994, *J Biol Chem* 269 (11):7835-8). In addition, DARC/ACKR1 receptor has also been shown to regulate transcytosis of the bound ligands in endothelial cells (Nibbs and Graham 2013, *Nat Rev Immunol* 13 (11): 815-29), influencing leukocyte trafficking and the ability of the receptor to maintain homeostatic chemokine levels (Pruenster et al. 2009, *Nat Immunol* 10 (1):101-8). A population-private DARC/ACKR1 gene mutation, defined as DARC/ACKR1$^{es(erythrocyte\ silent)}$, removes expression of DARC/ACKR1, specifically on erythrocytes, and is also known as the extensively characterized "Duffy-null blood group". This mutation is mostly restricted to populations of West African descent and remains fixed (100% allele frequency) in present-day populations within west and central Sub-Saharan Africa.

The present disclosure defines a set of significant clinical associations of DARC/ACKR1 alleles among patient demographics that are associated with clinical outcomes and that may inform the decisions for oncologic use of immunotherapy treatments. The teachings of the present disclosure can be used to decrease tumor-subtype disparities in incidence and mortality among race groups.

The term "Duffy-null" as used herein describes a specific gene mutation, i.e., a SNP in which the thymidine at position 159,204,893 of the wild-type gene ACKR1 (GenBank no. NG_011626.3) in the Genome Reference Consortium Human genome build GRCh38 38.1/142 is substituted by the nucleotide cytosine. Such a substitution in both alleles is defined as "Duffy-null". The reference SNP number is rs2814778. This mutation is tissue specific and results in a lack of protein expression of DARC/ACKR1 in red blood cells (RBCs). As an example, identification of Duffy-null may be carried out based on the presence of the specific SNP in the DNA, or corresponding/resulting changes of the protein on the surface of RBCs. The term Duffy-positive may be used for an individual who has at least one wild type allele of the gene ACKR1 with respect to the SNP on rs2814778 (i.e., the individual would have at least one allele that has T, not C at the relevant position in rs2814778. Kits to determine Duffy-null blood grouping are commercially available (e.g. HemoPlex Kidd and Duffy Genotyping Kit from Biofortuna, product no. HP8).

When the RBCs from an individual express DARC protein, the individual may be termed as RBC-DARC positive. When the tumor cells from an individual express the DARC protein, the individual may be termed as tumor-DARC positive.

The determination of the presence of Duffy-null (meaning an A to G substitution in reference to the template strand or a T to C substitution in reference to the coding strand in both alleles) can be made by any method known to those skilled in the art.

The terms T to C substitution and A to G substitution refers to the same mutation and is used herein interchangeably. The T to C substitution is used in reference to the coding strand (going from 5' to 3'), while the A to G substitution is used in reference to the template strand (going from 5' to 3'). The nucleotide that is substituted is shown below as underlined.

```
Sequence from coding strand =
                              (SEQ ID NO: 1)
    TCCTTGGCTCTTATCTTGGAAGCACAGGCG Sequence from template strand =
                              (SEQ ID NO: 2)
    CGCCTGTGCTTCCAAGATAAGAGCCAAGGA
```

The term "treatment" refers to reduction in one or more symptoms or features associated with the presence of the particular condition being treated. Treatment does not necessarily mean complete remission, nor does it preclude recurrence or relapses. For example, the present disclosure provides a method for reducing the size of a tumor or arresting the growth of a tumor or reducing or inhibiting the rate of growth of a tumor or tumor cells—all of which are considered as "treatment"—comprising administering to an individual in need of treatment, a therapeutically effective amount of a composition.

The term "therapeutically effective amount" as used herein is the amount sufficient to achieve, in a single or multiple doses, the intended purpose of treatment.

The term "therapies other than immune therapy" or other similar terms mean a therapy that does not include immune activating/enhancing therapies (such as checkpoint inhibitors or cell-based therapies) and can include chemotherapy, antibodies that target the tumor cells directly, radiation therapy, surgery, small molecules, or any combination thereof. The term "immunotherapy" and "immune therapy" are used interchangeably. Immune therapies include checkpoint inhibitors.

In an aspect, this disclosure provides a method for identifying an individual afflicted with cancer (such as breast cancer) as being suitable or not suitable for immune therapy, the method comprising testing for the expression of DARC protein in cells obtained from the individual. In an embodiment, the suitability of the individual for immune therapy administration is determined by testing for the Duffy-null mutation (as represented by rs2814778), which can be identified in any nucleated cell. The Duffy-null status corresponds to a lack of DARC protein expression in RBCs.

In an embodiment, this disclosure provides a method for identifying if an individual afflicted with cancer is or is not suitable for immune therapy comprising: testing for the presence or absence of Duffy-null mutation in the genome of a nucleated cell obtained from the individual, or the presence or absence of DARC protein on red blood cells from the individual; and if the Duffy-null mutation is present in both alleles, or if no DARC protein is detected on red blood cells, identifying the individual as not suitable for immune therapy, and if the Duffy null mutation is not present on both alleles (i.e., one or both alleles are wild type with respect to rs2814778), or if the RBCs express DARC protein, then identifying the individual as suitable for immune therapy. The testing for the presence of absence of Duffy-null mutation can be carried out by testing for a T to C substitution in rs2814778. Testing for expression of DARC protein can be carried out by immunohistochemistry, ELISA, Western blotting, or any other affinity binding or immunological technique.

In an embodiment, the if an individual is identified as being Duffy null or lacking expression of DARC on RBCs, a further step of determining if in the individual, the status of DARC expression in a tumor cell is the same as in the RBCs (i.e. that there is no expression) is performed. This is helpful because while there may be no DARC expression in RBCs in a Duffy-null individual, it may be expressed elsewhere, such as in a tumor cell (because the Duffy null mutation affects DARC expression in a tissue specific manner). So, even in a Duffy-null individual, if the tumor cells show expression of DARC, the individual could still be deemed suitable for immune therapy.

In an embodiment, the disclosure provides a method comprising identifying if an individual afflicted with cancer is suitable or not suitable for immune therapy comprising: testing for the presence or absence of Duffy-null mutation in the genome of cell obtained from the individual, or testing for the presence or absence of DARC protein on red blood cells from the individual, and if the Duffy-null mutation is present in both alleles, or if no DARC protein is detected on red blood cells, further testing the individual for one or more of the following characteristics: circulating CCL2 and CXCL8 levels are found to be at the same level as healthy controls, expression of DARC protein on the tumor cells, and a profile of tumor-associated leukocytes that is similar to the profile from a known (reference) tumor that is not Duffy-null, and if the any of the characteristics are present, then identifying the individual as being suited for immune therapy and any other cancer therapy, but if none of the characteristics are present, then identifying the individual as not suitable for immune therapy. If the Duffy null mutation is not present on both alleles, or if the RBCs express DARC protein, the individual as suitable for immune therapy or any other type of therapy.

In an aspect, this disclosure provides a method for treatment of an individual afflicted with cancer comprising: testing in a biological sample obtained from the individual, the presence or absence of genomic Duffy-null mutation, or the presence or absence of DARC protein on red blood cells from the individual;
a) if the Duffy-null mutation is present in both alleles, or if no DARC protein is detected on red blood cells, treating the individual with a treatment other than immune therapy; or
b) if the Duffy null mutation is not present on both alleles, or if DARC protein is detected on red blood cells, treating the individual with immune therapy or any treatment other than immune therapy.

In an embodiment, this disclosure provides a method for treatment of an individual afflicted with cancer comprising: testing in a biological sample obtained from the individual, the presence or absence of genomic Duffy-null mutation, or the presence or absence of DARC protein on red blood cells from the individual;
a) if the Duffy-null mutation is present in both alleles, or if no DARC protein is detected on red blood cells, further testing the individual for one or more of the following characteristics: circulating CCL2 and CXCL8 levels, expression of DARC protein on the tumor cells, and a profile of tumor-associated leukocytes that is similar to the profile from a known tumor that is not Duffy-null, and if CCL2 levels, or CXCL8 levels are found to be at the same level as healthy controls, expression of DARC protein on tumor cells is detected, or a tumor associated leukocyte profile similar to a profile from a known (reference) tumor that is not Duffy-null is observed, then treating the individual with a therapy comprising immune therapy, chemotherapy, antibodies that target the tumor cells directly, radiation therapy, surgery, or any combination thereof, but if none of the characteristics are detected then treating the individual with a treatment other than immune therapy; or
b) if the Duffy null mutation is not present on both alleles, or if DARC protein is detected on red blood cells, treating the individual with immune therapy or any treatment other than immune therapy.

Immune therapy as contemplated in any method described herein can comprise administration of checkpoint inhibitors. Examples of checkpoint inhibitors include antibodies that target PD-1, PD-L1, CTLA-4, LAG3, B7-H3, B7-H4, or TIM3. Examples include nivolumab, pembrolizumab, BMS-936559, MPDL3280A, ipilimumab, tremelimumab and the like.

In an embodiment, the expression of DARC in a tumor cell is detected by detecting the presence of DARC mRNA or DARC protein or a fragment thereof. The presence of Duffy null mutation in the genome of the individual can be tested in sample of the individual comprising nucleated cells. Such a sample includes, for example, blood, saliva, urine, any biological fluid, or tumor biopsy. A tumor expressing the DARC mRNA or protein is considered to be termed "DARC-positive".

In an embodiment, the disclosure provides a method for treatment of an individual afflicted with cancer who has been identified as being Duffy-null, and administering a treatment other than immunotherapy. The individual can be identified as Duffy-null by detecting the presence of Duffy-null mutation (rs2814778) in both alleles, or a lack of expression of DARC in the red blood cells. Alternatively, or additionally, the individual can be tested for one or more of the following characteristics: lower circulating CCL2 and/or higher circulating CXCL8 levels compared to controls, a lack of expression of DARC protein on the tumor cells, and a profile of tumor-associated leukocytes that is similar to the profile from a control (e.g. a reference value obtained from a tumor that is known to be Duffy-null). If any of the characteristics are present, then the individual can be administered a therapy other than immune therapy. Conversely, if one or more of the following opposite characteristics are present: similar circulating CCL2 and/or similar circulating CXCL8 levels compared to controls, presence of expression of DARC protein on the tumor cells, and a profile of tumor-associated leukocytes that is similar to the profile from a control (e.g. a reference value obtained from a tumor that is known to be not Duffy-null), then the individual may be administered immune therapy or any other anti-cancer therapy, such as, for example, chemotherapy, antibodies that target the tumor cells directly, radiation therapy, surgery, and/or small molecules.

The cancer may be a tumor and the tumor may be breast, ovarian, melanoma, bladder, lung, thyroid, pancreatic, prostate, uterine, testicular, gastric, soft tissue and osteogenic sarcomas, neuroblastoma, Wilms' tumor, malignant lymphoma (Hodgkin's and non-Hodgkin's), multiple myeloma, and tumor of the head, neck, cervix, colon, or vagina, or any other malignant tumor.

In an embodiment, the method comprises administering a treatment comprising immunotherapy, chemotherapy, antibodies that target the tumor cells directly, radiation therapy, surgery, small molecules or any combination thereof in an individual afflicted with cancer and who has been identified as not being Duffy-null, or who is genomic Duffy null, but expressed DARC in the tumor cells.

In an embodiment, the method comprises in an individual afflicted with cancer and who has been identified as being Duffy-null, but who exhibits one or more of the following characteristics: circulating CCL2 and CXCL8 levels similar to levels from healthy controls or individuals with known tumor that is not Duffy null, or a profile of tumor-associated leukocytes that is similar to the profile from a known (e.g. a reference value obtained from a tumor that is known to be not Duffy-null, administering a treatment comprising immunotherapy, chemotherapy, antibodies that target the tumor cells directly, small molecule inhibitors, radiation therapy, surgery, or any combination thereof.

In an embodiment, the disclosure provides a method for identifying if a tumor (such as a breast tumor) in an individual is likely to respond to immune therapy comprising detecting the presence of DARC in the tumor, and if the tumor is DARC positive (i.e., DARC is expressed), identifying the individual as likely to respond to immune therapy, and if no DARC is present in the tumor, then identifying the individual as not likely to respond to immune therapy. The DARC protein may be detected by an immunoassay. The DARC mRNA may be detected via a nucleic acid assay. If the individual is found likely to respond to immune therapy, the individual can be administered an effective amount of immune therapy. If an individual is found not likely to respond to immune therapy, the individual can be administered an effective amount of a therapy other than immune therapy to the individual. An example of immune therapy is checkpoint inhibitors.

Methods for detecting Duffy-null include any suitable criterion known in the art, including but not limited to DNA, mRNA, cDNA, proteins, protein fragments, or downstream markers that are indicative of changes to the genotype or phenotype. Examples of methods include whole genome sequencing, polymerase chain reaction (PCR) including quantitative real time PCR (qRT-PCR) and other amplification type detection methods, such as, for example, branched DNA, SISBA, TMA and the like, RNA-Seq, microarray analysis, gene expression profiling, and/or serial analysis of gene expression (SAGE), in situ hybridization, fluorescence in situ hybridization (FISH), immunohistochemistry (IHC), Western blot analysis, immunoprecipitation, molecular binding assays, ELISA, ELIFA, fluorescence activated cell sorting (FACS), MassARRAY, proteomics, and the like. These techniques are well known (see, for example, Ausubel et al. eds. (Current Protocols In Molecular Biology, 1995).

Examples of primers used to detect DARC mRNA b PCR amplification are:

```
Forward-
                              (SEQ ID NO: 3)
TCTGGGTATGTCCTCCAGGC

Reverse-
                              (SEQ ID NO: 4)
AAGGGCAGTGCAGAGTCATC

Forward-
                              (SEQ ID NO: 5)
TCCAATTTCCCAGCACCTCC

Reverse-
                              (SEQ ID NO: 6)
GGCTGGTTGGGACTACACTC
```

To determine whether the genome of an individual is Duffy-null, a biological sample from the individual can be obtained. The sample can be any biological sample containing the individual's DNA. Examples of such samples include blood, saliva, sweat, urine, tumor cells, any biological fluid, and epithelial cells. In general, the biological sample may be any biological material that contains DNA or RNA of the subject, such as a nucleated cell source. Non-limiting examples of cell sources include hair, skin, nucleated blood cells, buccal cells, any cells present in tissue obtained by biopsy or any other cell collection method. DNA may be extracted from the biologic sample such as the cell source or body fluid using any of the methods that are known in the art. The sample can be obtained by any method known to those in the art. Suitable methods include, for example, venous puncture of a vein to obtain a blood sample and cheek cell scraping to obtain a buccal sample, biopsy and the like.

DNA can be isolated from the sample by any method known to those in the art. For example, commercial kits, such as the QIAGEN System (QIAmp DNA Blood Midi Kit, Hilder, Germany) can be used to isolate DNA.

The DNA is optionally amplified by methods known in the art. One suitable method is the polymerase chain reaction (PCR) method described by Saiki et al., *Science* 239:487 (1988), U.S. Pat. No. 4,683,195 and Sambrook et al. (Eds.), Molecular Cloning, Third Edition, Cold Spring Harbor Laboratory Press, Cold Spring Harbor, New York (2001). For example, oligonucleotide primers complementary to a nucleotide sequence flanking and/or present at the site of the genetic alteration of the allele can be used to amplify the allele. The isolated DNA can be used to determine whether both alleles contain the substitution of A to G in the DARC/ACKR1 gene as described herein (Duffy-null).

The presence or absence of an allele containing a genetic alteration can be determined by any method known to those skilled in the art. One method is to sequence the isolated DNA and compare the sequence to that of wild-type ACKR1. Alternative methods include, for example, use of nucleic acid probes and PCR. Methods for making and using nucleic acid probes are well documented in the art. For example, see Keller G H and Manak M M, *DNA Probes, 2$^{nd}$ ed.*, Macmillan Publishers Ltd., England (1991) and Hames B D and Higgins S J, eds., Gene Probes I and Gene Probes II, IRL Press, Oxford (1995).

Genotyping (e.g., SNP genotyping) or sequencing may involve techniques that include allele specific oligonucleotide hybridization, size analysis, sequencing, hybridization, 5' nuclease digestion, single-stranded conformation polymorphism analysis, allele specific hybridization, primer specific extension, and oligonucleotide ligation assays and the like.

As an example, the sequence of the extracted nucleic acid of the subject may be determined by any means known in the art, including but not limited to direct sequencing, hybridization with allele-specific oligonucleotides, allele-specific PCR, ligase-PCR, HOT cleavage, denaturing gradient gel electrophoresis (DDGE), and single-stranded conformational polymorphism (SSCP) analysis. Direct sequencing may be carried out by any method, such as, for example, chemical sequencing, using the Maxam-Gilbert method, by enzymatic sequencing, using the Sanger method; mass spectrometry sequencing; and sequencing using a chip-based technology. For example, DNA from an individual can be subjected to amplification by PCR using specific amplification primers.

Restriction fragment length polymorphism (RFLP) analysis can be used for determining the presence or absence of a particular allele (Jarcho et al. in Dracopoli et al., Current Protocols in Human Genetics pages 2.7.1-2.7.5, John Wiley & Sons, New York; Innis et al., (Ed.), PCR Protocols, San Diego: Academic Press. Inc. (1990)). RFLP refers to any method for distinguishing genetic polymorphisms using a restriction enzyme, which is an endonuclease that catalyzes the degradation of nucleic acid and recognizes a specific base sequence, generally a palindrome or inverted repeat.

Allele-specific oligonucleotide hybridization can be used to detect an allele. Allele-specific oligonucleotide hybridization is based on the use of a labeled oligonucleotide probe having a sequence perfectly complementary, for example, to the sequence encompassing the allele. Under appropriate conditions, the allele-specific probe hybridizes to a nucleic acid containing the allele but not to other alleles, which have one or more nucleotide mismatches as compared to the probe. If desired, a second allele-specific oligonucleotide probe that matches an alternate allele also can be used. Further, allele-specific oligonucleotide amplification can be used to selectively amplify the particular allele by using an allele-specific oligonucleotide primer that is complementary to the nucleotide sequence of the particular allele.

A heteroduplex mobility assay (HMA) can be used to detect a SNP or a haplotype. HMA is useful for detecting the presence of a polymorphic sequence since a DNA duplex carrying a mismatch has reduced mobility in a polyacrylamide gel compared to the mobility of a perfectly base-paired duplex (Delwart et al., Science 262:1257-1261 (1993); White et al., Genomics 12:301-306 (1992)).

Single strand conformational, polymorphism (SSCP) can be used to detect the presence or absence of a SNP and/or a haplotype (see Hayashi, K., Methods Applic. 1:34-38 (1991)). This technique can be used to detect mutations based on differences in the secondary structure of single-strand DNA that produce an altered electrophoretic mobility upon non-denaturing gel electrophoresis. Polymorphic fragments are detected by comparison of the electrophoretic pattern of the test fragment to corresponding standard fragments containing known alleles.

Denaturing gradient gel electrophoresis (DGGE) can be used to detect a SNP and/or a haplotype. In DGGE, double-stranded DNA is electrophoresed in a gel containing an increasing concentration of denaturant; double-stranded fragments made up of mismatched alleles have segments that melt more rapidly, causing such fragments to migrate differently as compared to perfectly complementary sequences (Sheffield et al., "Identifying DNA Polymorphisms by Denaturing Gradient Gel Electrophoresis" in Innis et al., supra, 1990).

Other methods for determining the presence or absence of a SNP and/or a haplotype include automated sequencing and RNAase mismatch techniques (Winter et al., Proc. Natl. Acad. Sci. 82:7575-7579 (1985)).

In certain embodiments, the presence and/or expression level/amount of DARC protein can be examined using ELISA, Western blotting, immunohistochemistry or other similar techniques for the detection of specific proteins or fragments. Generally, these techniques use affinity binding of the protein or fragments and then detection of the bound complex. Antibodies to DARC protein are commercially available (such as from Novus).

Once an individual is identified as being suitable for an immune therapy or other therapy, the individual can be treated with that therapy. Administration of therapies, such as immune therapies, anti-cancer antibody molecules, chemotherapy, other anti-cancer therapies (e.g., targeted anti-cancer therapies, gene therapy, viral therapy, small molecule inhibitors, RNA therapy, bone marrow transplantation, nanotherapy, or oncolytic drugs), hormone therapy, cytotoxic agents, surgical procedures (e.g., lumpectomy or mastectomy) and/or radiation procedures, or a combination of any of the foregoing, can be carried out by methods known in the art.

Examples of cytotoxic agents include antimicrotubule agents, topoisomerase inhibitors, anti-metabolites, mitotic inhibitors, alkylating agents, anthracyclines, vinca alkaloids, intercalating agents, agents capable of interfering with a signal transduction pathway, agents that promote apoptosis, proteosome inhibitors. Other therapies include targeting one or more proteins of the PI3K/AKT/mTOR pathway, an HSP90 inhibitor, or a tubulin inhibitor. Radiation can be local or whole body irradiation (e.g., gamma irradiation). Hormone therapy generally includes agents that lower certain hormone levels. For example, hormone therapy is useful for ER+ metastatic breast cancer. Hormone therapy relating to estrogen includes agents that interfere with estrogens ability to stimulate the growth of breast cancer cells. Selective Estrogen Receptor Modulators (SERMs) bind to estrogen receptors to prevent estrogen binding. Examples include tamoxifen (Nolvadex®), raloxifene (Evista®) and toremifene (Fareston®). Selective Estrogen Receptor Downregulators (SERDs) work to block the effect of estrogen on cells. Examples include fulvestrant (Faslodex®).

Examples of chemotherapeutic agents include doxorubicin, daunorubicin, gemcitabine, epirubicin, topotecan, vincristine, mitoxantrone, ciprofloxacin, cisplatin, erlotinib, docetaxel 5-FU (fluorouracil, 5-fluorouracil), carboplatin, paclitaxel, trastuzumab, temozolomide, Akti-1/2, HPPD, rapamycin, oxaliplatin, bortezomib, sutent, letrozole, imatinib mesylate, XL-518, ARRY-886, SF-1126, BEZ-235, leucovorin, lapatinib, lonafarnib, sorafenib, gefitinib, irinotecan, tipifarnib, vandetanib, chloranmbucil, temsirolimus, pazopanib, canfosfamide, thiotepa and cyclosphosphamide and others. Examples of anti-cancer agents are provided in U.S. Patent application publication 20160376659, which description is incorporated herein by reference. Examples of anticancer antibodies include rituximab (Rituxan® or MabThera®), cetuximab (Erbitux®), Vectibix (Panitumumab), Arzerra (Ofatumumab), Benlysta (belimumab), Perjeta (Pertuzumab), Dacetuzumab, and Blinatumomab, or others, or a functional fragment thereof.

For individuals whose tumors are identified as not being Duffy-null, or whose tumors are Duffy-positive, immunotherapy can be used, such as the use of checkpoint inhibitors. Additionally or alternatively, any of the therapies suitable for Duffy-null individuals can be used.

The terms "immune checkpoint blocker" or "checkpoint inhibitor" or "immune checkpoint inhibitor" may be used interchangeably and refers to a molecule(s) that reduces, inhibits, interferes with, or modulates one or more checkpoint proteins. A checkpoint inhibitor may be an antibody, or fragment thereof, antibody mimic, or small molecule that disrupts inhibitory signaling associated with the immune signal/response. For example, an inhibitor may inhibit or prevent interaction between PD-1 and PD-L1, between CTLA-4 and CD80 or CD86, between LAG3 and MHC class II molecules, and/or between TIM3 and galectin 9. In contrast to therapeutic antibodies which target tumor cells directly, immune checkpoint inhibitors enhance endogenous anti-tumor activity. In embodiments, a checkpoint inhibitor suitable for use in individuals who are not Duffy-null include an antibody that targets, for example, PD-1, PD-L1, CTLA-4, LAG3, B7-H3, B7-H4, and TIM3. Examples of antibodies that target PD-1 include, e.g., nivolumab and pembrolizumab. Antibodies that target PD-L1 include BMS-936559 (Bristol-Myers Squibb) and MPDL3280A (Genetech). Antibodies that target CTLA-4 include ipilimumab, and tremelimumab. Some examples are provided in U.S. Pat. No. 10,166,273, the description of which is incorporated herein by reference.

In an embodiment, the method comprises determining the likelihood of having a poor outcome in individuals afflicted with breast cancer or any other type of solid tumor by testing for the Duffy-null allele (rs2814778) (i.e., the individual is homozygous (G/G) for the Duffy-null allele) and/or the DARC/ACKR1 protein. If the Duffy-null allele is present or the DARC/ACKR1 protein is absent in RBCs, then the individual is likely to have a poor outcome to immune therapy. If an individual is homozygous for the wild-type (A/A) allele or whose tumors have high DARC protein expression, the likelihood of responding to immune therapy is high and the individual is considered suitable for such treatment. The likelihood of a favorable response to immune therapy is intermediate in individuals who are heterozygous (A/G) for the Duffy-null allele or whose tumor has low to moderate DARC protein expression.

In an embodiment, the method is used to determine the immunogenicity of an individual's breast tumor or any other solid tumor type by looking at DARC phenotype and/or genotype. The tumor's protein, mRNA, or DNA can be collected and analyzed for DARC expression or Duffy-null genotype. The tumor's immunogenicity is high when DARC expression is detected or the Duffy-null genotype is not present and the tumor's immunogenicity is low if DARC expression is not detected or the Duffy-null genotype is present.

In an embodiment, the method of identifying individuals afflicted with cancer who is likely to respond to immunotherapy comprises analyzing that individual's DNA. The DNA can be obtained from blood, saliva, a mouth swab, urine or any other suitable source. The individual's DNA is analyzed for the Duffy-null genotype (rs2814778). Based on the individuals genotype appropriate therapies can be administered as described herein.

In an embodiment, the method of identifying individuals afflicted with cancer who is likely to respond to immunotherapy comprises testing the individual's red blood cells. The RBCs can be obtained from a blood sample. This can be the same blood sample used for the analysis for Duffy-null genotype or it can be a separate blood sample. The individual's RBCs are analyzed for the Duffy-null phenotype using antibodies specific for the DARC protein. Based on the individual's phenotype appropriate therapies can be administered as described herein.

In an embodiment, the method of identifying individuals afflicted with cancer who are likely to respond to immunotherapy comprises analyzing an individual's serum or plasma. The serum or plasma is obtained from a blood sample. This can be the same blood sample used for the RBC analysis or for Duffy-null phenotype or it can be a separate blood sample. The individual's serum or plasma is analyzed for circulating levels of chemokines and/or cytokines that can include but are not limited to CCL2 and CXCL8. The individual's cytokines/chemokines can be analyzed in a large panel comprising a range of 4-100 analytes or they can be analyzed individually. Examples of suitable methods include ELISA, Western blot, Luminex chemokine assays, and other cytokine/chemokine bead-based flow cytometry detection methods. Based on the individuals circulating CCL2 and/or CXCL8 levels a suitable immunotherapy can be administered or other suitable anti-cancer therapies can be administered as described herein.

In one embodiment, the method of identifying individuals afflicted with cancer who is likely to respond to immunotherapy comprises analyzing an individual's tumor. Tumor associated leukocytes (TAL) can be collected from the tumor sample and a TAL profile can be generated that defines all of the immune cell types found in the individual's tumor. Alternatively, mRNA can be isolated from the tumor and gene expression profiling performed identifying genes specific for each immune cell type of interest. Based on the individual's TAL profile a suitable immunotherapy can be administered or other suitable anti-cancer therapies can be administered as described herein.

In an embodiment, tumor cells can also be analyzed for DARC expression by using immunofluorescence or immunohistochemical techniques.

In an embodiment, the method of identifying individuals afflicted with cancer who is likely to respond to immunotherapy comprises a combination of analyzing an individual's tumor and analyzing the individual's serum or plasma. Tumor samples can be stained for DARC expression using antibodies and immunofluorescence or immunohistochemical techniques. Alternatively analyzing tumor mRNA for DARC expression can be performed. Circulating cytokine/chemokine levels can also be measured in the individual's serum. Examples of cytokines/chemokines include CCL2 and CXCL8 but other cytokines may be measured as well. Identifying tumor DARC biomarker expression and circulating cytokine/chemokine levels can identify which individuals are suitable to receive immunotherapy. Individuals who are not suitable for immunotherapy (e.g. Duffy-null individuals) can be given suitable alternative anti-cancer therapies.

In an embodiment, the disclosure provides a method of identifying individuals afflicted with cancer who are not likely to respond to immunotherapy. The method comprises of genotyping/phenotyping a biological fluid sample (e.g., blood, saliva, urine etc) to identify for Duffy-null, measuring circulating cytokine/chemokine (such as CCL2 and CXCL8), detecting DARC protein expression in an individual's tumor (such as tumor epithelial cells), determining the profile of tumor-associated leukocytes in an individual's tumor sample, or any combination of the above.

In an embodiment, the method comprises genotyping/phenotyping a biological fluid sample (e.g., blood, saliva, urine etc) to detect for the presence of Duffy-null, in combination with one or more of the following: a) measuring circulating cytokine/chemokine (such as CCL2 and CXCL8), b) detecting DARC protein expression in an individual's tumor (such as tumor epithelial cells), and c) determining the profile of tumor-associated leukocytes in an individual's tumor sample, or any combination of the above.

Based on our findings the present disclosure provides methods for identifying and prognosticating individuals that would and would not benefit from immunotherapies for cancers such as solid tumors from breast, colorectal, kidney, ovarian, and any other cancers. The method comprises steps for identifying individuals who would benefit from immunotherapy based on their genetic disposition; the genetic disposition of the tumor; and/or circulating chemokine levels and then administering a suitable immunotherapy or any other non-immunotherapy to that individual. Immuno- and non-immunotherapies may include T cell therapies, cytokine based therapies, antibody (Ab) based therapies, small molecule inhibitor therapies, chemotherapies, and radiation therapies.

In any of the embodiments, administration of immunotherapy to an individual having a DARC expressing tumor may comprise administration of a checkpoint inhibitor.

The steps of the method described in the various examples disclosed herein are sufficient to carry out the methods of the present invention. Thus, in an example, the method consists essentially of a combination of the steps of the methods disclosed herein.

The following statements are provided to illustrate embodiments.

Statement 1. In an individual afflicted with cancer and who has been identified as being Duffy-null, administering a treatment other than immunotherapy.

Statement 2. The method of Statement 1, wherein the treatment other than immunotherapy comprises one or more of chemotherapy, antibodies that target the tumor cells directly, radiation therapy, surgery, and other anti-cancer therapies.

Statement 3. The method of Statement 1, wherein the individual has been identified as being Duffy-null by detecting the presence of Duffy-null mutation (rs2814778) in both alleles, or a lack of expression of DARC in the red blood cells.

Statement 4. The method of Statement 3, wherein the individual has been further identified as having one or more of the following characteristics: lower circulating CCL2 and/or higher circulating CXCL8 levels compared to controls, a lack of expression of DARC protein on the tumor cells, and a profile of tumor-associated leukocytes that is similar to the profile from a control (e.g. a reference value obtained from a tumor that is known to be not Duffy-null).

Statement 4a. The method of Statement 4, wherein a lack of expression of DARC in tumor cells is determined by testing for the DARC mRNA or DARC protein or a fragment thereof.

Statement 5. The method of Statement 1, wherein the cancer is a tumor comprising breast, ovarian, melanoma, bladder, lung, thyroid, pancreatic, prostate, uterine, testicular, gastric, soft tissue and osteogenic sarcomas, neuroblastoma, Wilms' tumor, malignant lymphoma (Hodgkin's and non-Hodgkin's), multiple myeloma, and tumor of the head, neck, cervix, colon, or vagina, or any other malignant tumor.

Statement 6. In an individual afflicted with cancer and who has been identified as not being Duffy-null, administering a treatment comprising immunotherapy, chemotherapy, antibodies that target the tumor cells directly, radiation therapy, surgery, or any combination thereof.

Statement 6a. The method of Statement 6, wherein immunotherapy comprises administration of checkpoint inhibitors.

Statement 6b. The method of Statement 6a, wherein the checkpoint inhibitors comprise: an antibody that targets PD-1, PD-L1, CTLA-4, LAG3, B7-H3, B7-H4, or TIM3.

Statement 6c. The method of 6b, wherein the antibody that targets PD-1 is nivolumab or pembrolizumab.

Statement 6d. The method of 6b, wherein the antibody that targets PD-L1 is BMS-936559 or MPDL3280A.

Statement 6e. The method of Statement 6b, wherein the antibody that targets CTLA-4 is ipilimumab, or tremelimumab.

Statement 7. The method of Statement 6, wherein the individual has been identified as not being Duffy-null by detecting a lack of the Duffy-null mutation on both or one allele(s) or detecting expression of DARC in the red blood cells.

Statement 8. In an individual afflicted with cancer and who has been identified as being Duffy-null, but who exhibits one or more of the following characteristics: circulating CCL2 and CXCL8 levels (such as no change in CCL2 or CXCL8 compared to healthy controls or individuals with known tumor that is not Duffy null), expression of DARC protein on the tumor cells, and a profile of tumor-associated leukocytes that is similar to the profile from a known (e.g. a reference value obtained from a tumor that is known to be Duffy-null) tumor not being Duffy-null, administering a treatment comprising immunotherapy, chemotherapy, antibodies that target the tumor cells directly, small molecule inhibitors, radiation therapy, surgery, or any combination thereof.

Statement 9. The method of Statement 6 or Statement 8, wherein the cancer is a tumor comprising breast, ovarian, melanoma, bladder, lung, thyroid, pancreatic, prostate, uterine, testicular, gastric, soft tissue and osteogenic sarcomas, neuroblastoma, Wilms' tumor, malignant lymphoma (Hodgkin's and non-Hodgkin's), multiple myeloma, and tumor of the head, neck, cervix, colon, or vagina, or any other malignant tumor.

Statement 10. A method of identifying an individual afflicted with cancer as being suitable or not suitable for immunotherapy comprising:
  i) Testing for the presence or absence of Duffy-null mutation in the genome of cells obtained from the individual, or the presence or absence of DARC protein on red blood cells from the individual;
  ii) If the Duffy-null mutation is present in both alleles, or if no DARC protein is detected on red blood cells, identifying the individual as a RBC-DARC negative individual and as an individual not suitable for immunotherapy, and if the Duffy-null mutation is not present on one or both alleles, or if the RBCs express DARC protein, then identifying the individual as suitable for immunotherapy.

Statement 11. The method of Statement 10, wherein the testing for the presence or absence of Duffy-null mutation is carried out by testing for a T to C substitution in rs2814778.

Statement 12. The method of Statement 10, wherein testing for expression of DARC protein is carried out by immunohistochemistry, ELISA, Western blotting, or any other affinity binding or immunological technique.

Statement 13. A method of identifying an individual afflicted with cancer as being suitable or not suitable for immunotherapy comprising:

i) Testing for the presence or absence of Duffy-null mutation in the genome of cell obtained from the individual, or the presence or absence of DARC protein on red blood cells from the individual;

ii) If the Duffy-null mutation is present in both alleles, or if no DARC protein is detected on red blood cells, further testing the individual for one or more of the following characteristics: circulating CCL2 and CXCL8 levels (such as no change in CCL2 or CXCL8 compared to healthy controls or in individuals who are known to have a tumor that is not Duffy null), expression of DARC protein on the tumor cells, and a profile of tumor-associated leukocytes that is similar to the profile from a known (e.g. a reference value obtained from a tumor that is known to be Duffy-null) tumor that is not Duffy-null, and if any of the characteristics are present, then identifying the individual as being suited for immunotherapy and any other cancer therapy, but if none of the characteristics are present, then identifying the individual as not suitable for immunotherapy; and if the Duffy-null mutation is not present on both alleles, or if the RBCs express DARC protein, then identifying the individual as suitable for immunotherapy.

Statement 13a. The method of Statement 13, wherein the testing for expression of DARC protein or determining levels of circulating CCL2 or CXCL8 is carried out by immunohistochemistry, ELISA, Western blotting, or any other affinity binding or immunological technique.

Statement 14. A method of treating an individual afflicted with cancer comprising:

i) in a biological sample obtained from the individual, testing for the presence or absence of genomic Duffy-null mutation, or the presence or absence of DARC protein on red blood cells from the individual;

ii) if the Duffy-null mutation is present in both alleles, or if no DARC protein is detected on red blood cells, treating the individual with a treatment other than immunotherapy;

iii) if the Duffy-null mutation is not present on both alleles, or if DARC protein is detected on red blood cells, treating the individual with immunotherapy or any treatment other than immunotherapy.

Statement 15. The method of Statement 14, wherein the treatment other than immunotherapy comprises chemotherapy, antibodies that target the tumor cells directly, small molecule inhibitors, radiation therapy, surgery, or any combination thereof.

Statement 16. The method of Statement 14, further comprising after i), testing the individual for one or more of the following characteristics: circulating CCL2 and CXCL8 levels, expression of DARC protein on the tumor cells, and a profile of tumor-associated leukocytes that is similar to the profile from a known tumor that is not Duffy-null, and if CCL2 levels, or CXCL8 levels are found to be at the same level as healthy controls, expression of DARC protein on tumor cells is detected, or a tumor associated leukocyte profile similar to a profile from a known (e.g. a reference value obtained from a tumor that is known to be not Duffy-null) tumor that is not Duffy-null is observed, then treating the individual with a therapy comprising immunotherapy, chemotherapy, antibodies that target the tumor cells directly, small molecule inhibitors, radiation therapy, surgery, or any combination thereof.

Statement 17. The method of any of Statements 10-16, wherein immunotherapy comprises administration of checkpoint inhibitors.

Statement 17a. The method of Statement 17, wherein the checkpoint inhibitors comprise: an antibody that targets PD-1, PD-L1, CTLA-4, LAG3, B7-H3, B7-H4, or TIM3.

Statement 17b. The method of 17a, wherein the antibody that targets PD-1 is nivolumab or pembrolizumab.

Statement 17c. The method of 17a, wherein the antibody that targets PD-L1 is BMS-936559 or MPDL3280A.

Statement 17d. The method of Statement 17a, wherein the antibody that targets CTLA-4 is ipilimumab, or tremelimumab.

Statement 18. The method of any of the foregoing Statements, wherein the expression of DARC in tumor cells is detected by detecting the presence of DARC mRNA or DARC protein or a fragment thereof.

Statement 19. The method of any of the foregoing Statements, wherein the presence of Duffy-null mutation in the genome of the individual is tested in a sample of the individual comprising nucleated cells.

Statement 20. The method of Statement 19, wherein the sample is blood, saliva, urine, any biological fluid or tissue, or tumor biopsy.

Statement 21. A method for identifying if a tumor in an individual is likely to respond to immune therapy comprising detecting the presence of DARC in the tumor, and if the tumor is DARC positive (i.e., DARC is expressed), identifying the individual as likely to respond to immune therapy, and if no DARC is present in the tumor, then identifying the individual as not likely to respond to immune therapy.

Statement 22a. The method of Statement 21, if an individual is found likely to respond to immune therapy, further comprising administering an effective amount of immune therapy to the individual.

Statement 22b. The method of Statement 21, if an individual is found not likely to respond to immune therapy, further comprising administering an effective amount of a therapy other than immune therapy to the individual.

Statement 23. The method of Statement 21 or 22, wherein the DARC protein is detected by an immunoassay.

Statement 24. The method of Statement 21 or 22, wherein the DARC mRNA is detected via a nucleic acid assay.

Statement 25. The method of Statement 22a, wherein the immune therapy is a checkpoint inhibitor.

Statement 26. The method of any of Statements 21-25, wherein the tumor is a breast tumor.

The following example is presented to illustrate the present disclosure. It is not intended to be limiting in any matter.

Example 1

Tumor-specific immune response is an important aspect of disease prognosis and ultimately impacts treatment decisions for innovative immunotherapies. The Atypical Chemokine Receptor 1 (ACKR1/DARC) gene, plays a pivotal role in immune regulation and harbors several Single Nucleotide Variants (SNVs) that are specific to Sub-Saharan African Ancestry. In this example, we describe the clinical relevance of DARC/ACKR1 tumor expression in breast cancer, in the context of a tumor immune response that may be associated with Sub-Saharan African Ancestry. We found that infiltrating carcinomas from The Cancer Genome Atlas (TCGA) breast cohort (n=838) that African-Americans (AA) have a higher proportion of tumors with low DARC/ACKR1— expression when compared to White Americans (WA), and DARC/ACKR1 subgroups in tumors are positively correlated with pro-inflammatory chemokines, CCL2/MCP-1 ($p<0.0001$) and anti-correlated with CXCL8/IL-8 ($p<0.0001$). Sub-Saharan African-specific DARC/ACKR1 mutations appear to drive these correlations in cases, as evidenced by DARC/ACKR1 genotyping and phenotyping in our case-control cohort (n=422). Relapse-free survival (RFS) and overall survival (OS) were significantly longer in individuals with DARC/ACKR1-high tumors ($p<1.0\times10^{-16}$ and $p<2.2\times10^{-6}$, respectively) across all molecular tumor subtypes. Using CIBERSORT, we identified distinct immune cell profiles associated DARC/ACKR1 tumor expression and race with increased macrophage subtypes and regulatory T-cells in DARC/ACKR1-high tumors of AAs.

Materials and Methods

Study Design, Biospecimens and Cohort Summary

All biospecimens used in this study were obtained under one of two IRB approved protocols from either the University of Georgia (IRB ID: MOD00003730) or Henry Ford Health Systems (IRB ID: 4825). All research was performed in accordance with these guidelines, and all participants signed an informed consent to participate and donate blood, saliva, and/or tissue for this study.

Gene Expression and DARC/ACKR1 Subtype Analyses.

Gene expression levels were obtained from RNAseq data accessed through the web-portal of The Cancer Genome Atlas Breast Cancer cohort (n=838, 167 African Americans, 671 White Americans), https://cancergenome.nih.gov. After filtering samples for tissue status (removing samples that were normal tissue and metastatic tumors), histological findings (removing samples that were annotated as 'other', metaplastic, or non-infiltrating), we conducted linear regression analyses for gene correlations, stratified as indicated for specific contexts of interactions (i.e. molecular subtypes/phenotypes) and nominal logistical regressions across derived tumor status. For DARC/ACKR1 subtype analyses, DARC/ACKR1 expression (FIG. 1A) was stratified based on quartile ranking and shown as high (upper 30th quartile), medium (intermediate quartile) and low (lower 30th) categories (FIG. 1B). DARC/ACKR1 subtypes were then measured for associations with specific demographic or clinical variables by stratifying the population according to these variables (e.g. race and molecular breast cancer subtype, FIGS. 1C and D) and comparing distributions of DARC/ACKR1 subtypes within or among each category. We conducted multivariate modeling to assess effect estimates and adjust for demographic variables (i.e. race and age).

Cytokine Analysis with DARC/ACKR1 Subtypes.

The UCSC Xena Browser (http://xenabrowser.net, accessed April 2018) was used to generate a heat map of TCGA breast invasive carcinoma RNAseq gene expression data (IlluminaHiSeq, n=399) compared to a user-generated gene set of relevant cytokine genes (n=67, Table 1). Dichotomized DARC/ACKR1 positive (red) and negative (blue) subgroups were determined according to the values in Table 2. P-values for select cytokines were determined using Welch's t-test.

TABLE 1

Heat map Cytokine Gene List

| Geneset Name | Gene Names |
|---|---|
| All Cytokines (n = 67) | CXCL1 CXCL2 CXCL3 CXCL5 CXCL6 CXCL8 CXCL9 CXCL10 CXCL11 CXCL12 CXCL13 CXCL14 CXCL16 CXCL17 CCL1 CCL2 CCL3 CCL3L1 CCL3L3 CCL4L2 CCL5 CCL7 CCL8 CCL11 CCL13 CCL14 CCL16 CCL17 CCL18 CCL19 CCL20 CCL21 CCL22 CCL23 CCL26 CCL28 XCL1 XCL2 CX3CL1 IL18 IL18BP IL1A IL1B IL1F5 IL1RL2 IL1F9 IL33 TNFSF8 CD40LG CD70 TNFSF14 LTB TNFSF10 TNFSF11 TNFSF12 TNFSF13 TNFSF15 TNFSF4 IFNB1 IFNE IFNG CLCF1 CNTF IL11 IL6 LIF OSM |

TABLE 2

Heat map DARC/ACKR1 Gene Expression Range

| Designation | Color | Gene Expression Range |
|---|---|---|
| DARC/ACKR1 High | Red | 10.00 to 13.57 |
| DARC/ACKR1 Low | Blue | 0 to 4.00 |

Blood and Serum Specimens.

Figure 2:
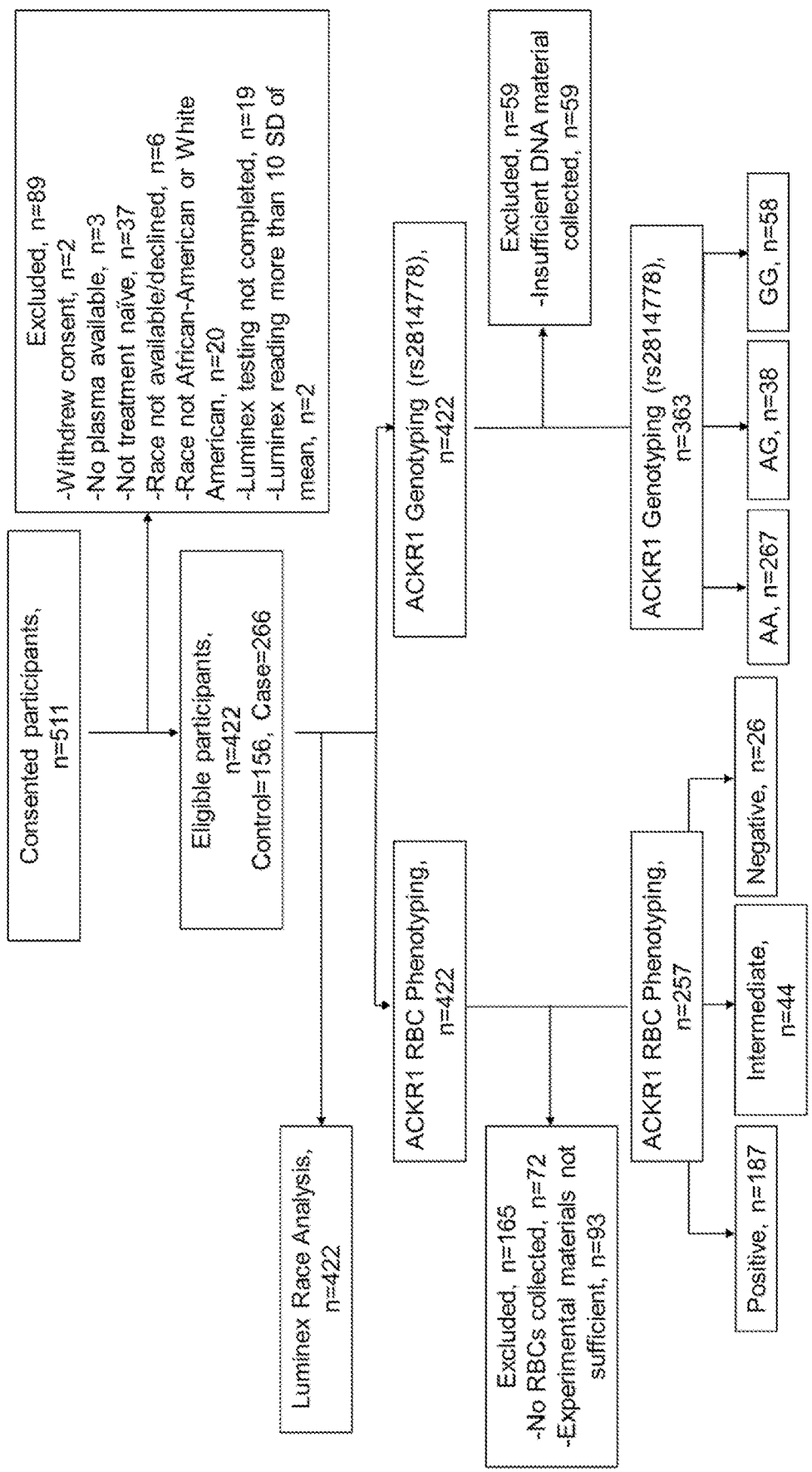
FIG. 2. Flowchart of cases and controls for study analysis. Of 511 consented participants, 422 (156 controls and 266 cases) were eligible for analysis. Participants excluded in analyses are denoted on the flowchart.

Following informed consent, and at time of enrollment or time of surgery, approximately 4 mL of blood was collected in EDTA-treated vacutainer tubes (BD) from each newly diagnosed patient pre-treatment at UCBC (n=41) and Henry Ford Health System (HIFHS) (n=225). Blood samples from non-cancer controls (n=67) and breast cancer survivors (n=17) were collected in a similar manner at time of enrollment at the University of Georgia (UGA) Clinical and Translational Research Unit (CTRU, Athens, Ga., n=84). All blood samples were processed within 24 hours of collection. Undiluted plasma was collected through centrifugation, and the remaining sample was separated via a Ficoll-plaque gradient (GE Healthcare) according to manufacturer's instructions. Serum control samples from pre-menopausal (n=31) and post-menopausal women (n=30) and breast cancer survivors (n=11) were purchased from the Susan G. Komen Tissue Bank (n=72). A flow chart detailing patient numbers and study exclusions can be found in FIG. 2.

Luminex Human Chemokine Multiplex Assay.

The multiplex assay was completed using patient undiluted plasma and serum. Plasma chemokine levels were quantified using the Bio-Plex Pro™ Human Chemokine Assay Kit (Bio-Rad) that was custom designed to measure the following chemokines and cytokines: CCL2/MCP-1, CXCL8/IL-8, CXCL9/MIG, CXCL1/Gro-α, IL-10. The assay was carried out following manufacturer's instructions, and the results were analyzed using the Bio-Plex Manager Software version 6.1.1. Statistical multivariate pairwise correlation analyses with these analytes can be found in Table 3.

TABLE 3

Pairwise analysis of analyte levels in undiluted plasma of study cohort compared to DARC/ACKR1 IHC Scores

| Variable | by Variable | Correlation | $R^2$ | Lower 95% | Upper 95% | Probability (p < 0.05) |
|---|---|---|---|---|---|---|
| DARC/ACKR1 IHC | CCL2/MCP-1 | 0.8605 | 0.7405 | 0.3959 | 0.9744 | 0.0061* |
| DARC/ACKR1 IHC | CXCL8/IL-8 | 0.7585 | 0.5753 | 0.1156 | 0.9535 | 0.0291* |
| DARC/ACKR1 IHC | CXCL9/MIG | 0.3554 | 0.1263 | −0.4659 | 0.8478 | 0.3875 |
| DARC/ACKR1 IHC | CXCL1/Gro-α | 0.4915 | 0.2415 | −0.3261 | 0.8885 | 0.2161 |
| DARC/ACKR1 IHC | IL-10/CSIF | 0.5620 | 0.3158 | −0.2362 | 0.9074 | 0.1471 |

*Refers to comparisons with significant correlations (p-values). Correlations are estimated by REML method.

Red Blood Cell Phenotyping by Immunofluorescence.

RBCs isolated from Ficoll-paque blood separation techniques are fixed in 4% PFA and stained with DARC/ACKR1 goat anti-human (Novus Biologicals) primary antibody and Alexa Fluor 488 chicken anti-goat (Invitrogen) fluorescent secondary antibody using standard immunofluorescence techniques. Positive plasma membrane control stains were done using CellMask™ Plasma Membrane Stain (Life Technologies) according to manufacturer's instructions. RBCs were imaged using a Keyence BZ fluorescent microscope at 40× magnification.

Duffy-Null Genotyping.

Genotyping for the Duffy-Null SNV, rs2814778, was performed using the Tagman™ GTXpress™ Master Mix and variant-specific probes (Applied Biosystems) according to manufacturer's instructions. Assay was read using an Applied Biosystems 7500 Fast Real-Time PCR System. Cohort allelic and genotypic frequencies compared to global populations from 1000 genomes data via ENSEMBL (www.ensembl.org) are provided in Table 4.

TABLE 4

Allelic and Genotypic Frequencies for rs2814778 across cohort compared to global averages (1000 genomes)

| | Allelic Frequency | | Genotypic Frequency | | |
|---|---|---|---|---|---|
| | A allele | G allele | A/A | A/G | G/G |
| Cohort (all) | 0.770 | 0.230 | 0.593 | 0.354 | 0.053 |
| Global (all) | 0.734 | 0.266 | 0.716 | 0.035 | 0.249 |
| Cohort (AA) | 0.181 | 0.819 | 0.033 | 0.297 | 0.671 |
| Global (AA, ASW) | 0.205 | 0.795 | 0.049 | 0.311 | 0.639 |
| Cohort (WA) | 0.993 | 0.007 | 0.987 | 0.013 | 0.000 |
| Global (WA, CEU) | 1.000 | 0.000 | 1.000 | 0.000 | 0.000 |

Tumor-Associated Leukocytes Gene Profiling.

The CIBERSORT online platform (Newman et al. 2015) was used to estimate the absolute fractions of 22 leukocyte populations in TCGA samples denoted as breast primary tumor samples. The analysis was run with 500 permutations, and quantile normalization disabled (as recommended by the tool for RNAseq data). Only those samples with a maximum significance value of p<0.05 were included in the final analysis (n=472).

Survival Analyses.

Figure 3:
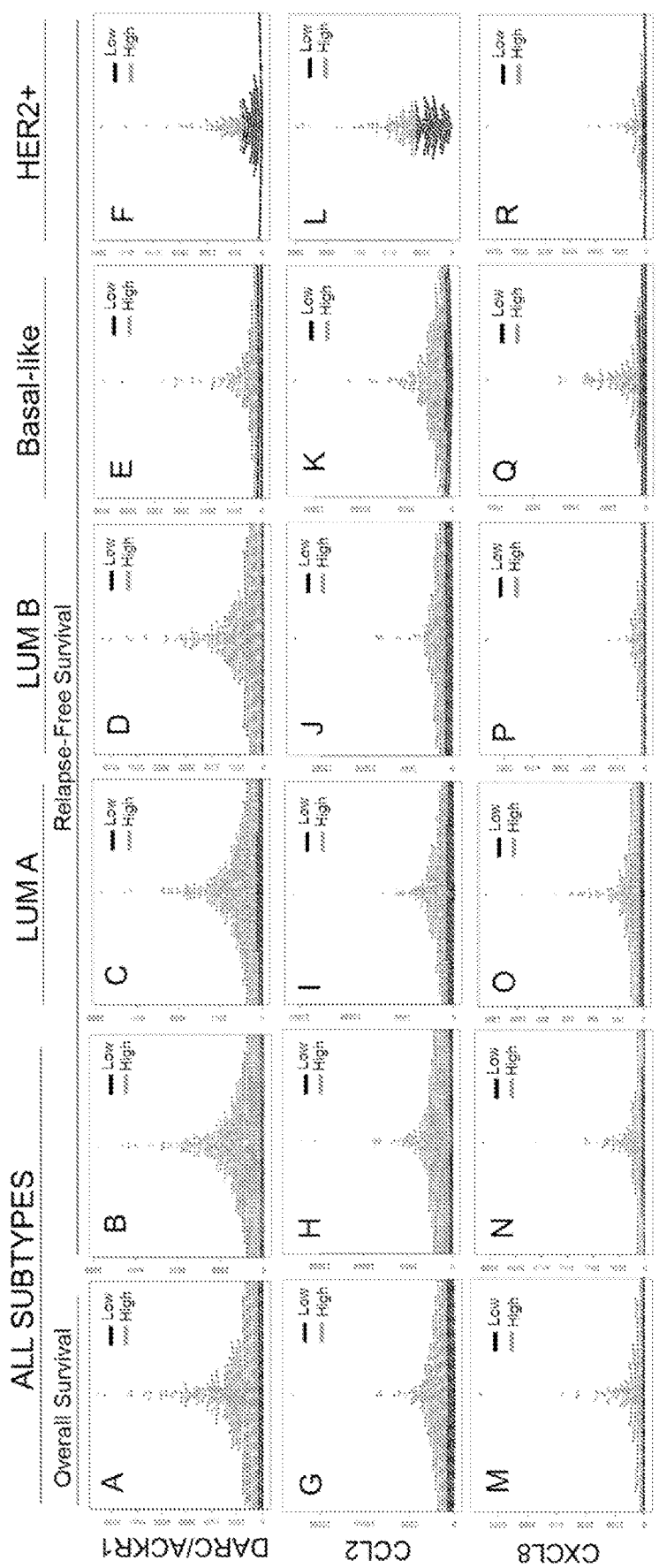
FIG. 3. Beeswarm distribution of KMplot survival curves. Beeswarm distributions demonstrating high (grey) and low (black) cutoff values for DARC/ACKR1 (top row, A-F), CCL2 (middle row, G-L), and CXCL8 (bottom row, M-R). Best cutoffs were automatically determined by the kmplots software.

Patient survival associations with gene expression data was calculated from 3,951 breast cancer patients. The data (Platforms: Affymetrix Microarrays: HG-U133A, HG-U133 Plus 2.0 and HG-U133A 2.0) were downloaded from GEO and AE databases (Gyorffy et al. 2010) (Table 5). Recurrence-Free Survival (RFS) and Overall Survival (OS) was assessed across all breast cancer subtypes and treatment types with dichotomized grouping for expression of DARC/ACKR1 (Probe ID: 208335_s_at), CCL2 (216598_s_at), and CXCL8 (211506_s_at) using the Kaplan-Meier (KM) plot application (Szasz et al. 2016) (http://kmplot.com). Distributions for high and low cutoff values (FIG. 3), p-values, hazard ratios, and confidence intervals for all survival analyses can be found in (Table 6).

TABLE 5

GEO microarray datasets from KM plotter survival analyses

| GEO ID | n= |
|---|---|
| GSE11121 | 200 |
| GSE12093 | 136 |
| GSE12276 | 204 |
| GSE1456 | 159 |
| GSE16391 | 55 |
| GSE16446 | 120 |
| GSE16716 | 47 |
| GSE17705 | 196 |
| GSE17907 | 54 |
| GSE18728 | 61 |
| GSE19615 | 115 |
| GSE20194 | 45 |
| GSE20271 | 96 |
| GSE2034 | 286 |
| GSE20685 | 327 |
| GSE20711 | 90 |
| GSE21653 | 240 |
| GSE2603 | 99 |
| GSE26971 | 276 |
| GSE2990 | 102 |
| GSE31448 | 71 |
| GSE31519 | 67 |
| GSE32646 | 115 |
| GSE3494 | 251 |
| GSE37946 | 41 |
| GSE41998 | 279 |
| GSE42568 | 121 |
| GSE45255 | 139 |
| GSE4611 | 153 |
| GSE5327 | 58 |
| GSE6532 | 82 |
| GSE7390 | 198 |
| GSE9195 | 77 |
| E-MTAB-365 | 537 |
| E-TABM-43 | 37 |
| Total | 5134 |

TABLE 6

Survival Analysis-Hazard Ratios, Confidence Intervals, and p-values

| Survival | Gene | Hazard Ratios | Confidence Interval | P-value |
|---|---|---|---|---|
| OS (All Subtypes) | DARC/ACKR1 | 0.60 | 0.48-0.74 | $2.2 \times 10^{-6}$ |
|  | CCL2 | 0.83 | 0.67-1.03 | 0.091 |
|  | CXCL8 | 1.45 | 1.14-1.84 | 0.0023 |
| RFS (All Subtypes) | DARC/ACKR1 | 0.62 | 0.56-0.70 | $1.0 \times 10^{-6}$ |
|  | CCL2 | 1.07 | 0.95-1.21 | 0.27 |
|  | CXCL8 | 1.35 | 1.20-1.52 | $7.7 \times 10^{-7}$ |
| RFS (Lum A) | DARC/ACKR1 | 0.63 | 0.53-0.75 | $9.1 \times 10^{-8}$ |
|  | CCL2 | 1.13 | 0.95-1.34 | 0.16 |
|  | CXCL8 | 1.17 | 0.99-1.39 | 0.067 |
| RFS (Lum B) | DARC/ACKR1 | 0.64 | 0.52-0.78 | $6.3 \times 10^{-6}$ |
|  | CCL2 | 0.80 | 0.65-0.98 | 0.028 |
|  | CXCL8 | 1.08 | 0.87-1.33 | 0.49 |
| RFS (Basal-like) | DARC/ACKR1 | 0.71 | 0.55-0.93 | 0.011 |
|  | CCL2 | 0.71 | 0.54-0.92 | 0.0098 |
|  | CXCL8 | 1.68 | 1.28-2.20 | 0.00014 |
| RFS (HER2+) | DARC/ACKR1 | 0.70 | 0.45-1.10 | 0.12 |
|  | CCL2 | 0.44 | 0.29-0.67 | $1.0 \times 10^{-4}$ |
|  | CXCL8 | 0.52 | 0.33-0.83 | 0.0053 |

All hazard ratios, confidence intervals, and p-values were annotated from www.kmplot.com.

Clinical Tumor Specimens.

Primary breast tumor specimens were acquired from the University Cancer and Blood Center (UCBC, n=8) in Athens, Ga., USA. UCBC patients were newly diagnosed (within ~1 month), and following informed consent at time of enrollment, primary tumor samples were collected at local Athens area hospitals. There were no exclusion criteria for this study cohort, which consisted of a racially diverse patient group having various molecular subtypes of breast cancer (Table 7). Tumor grade was determined using WHO guidelines, as well as the Ellis & Elston system of histologic grading. Clinical staging was evaluated using the TNM staging system maintained by AJCC (American Joint Committee on Cancer) and UICC (Union for International Cancer Control) following the most current NCCN guidelines at time of staging. Molecular breast cancer subtypes were determined using immunohistochemical (IHC) staining for estrogen receptor (ER), progesterone receptor (PR), and human epidermal growth factor receptor-2 (HER2) on the surface of the primary breast tumor.

Immunohistochemistry.

Formalin-Fixed Paraffin-Embedded tumor blocks were obtained from local Athens-area hospitals through UCBC. Subsequent slide preparations were conducted through the University of Georgia's Histology Core, using standard operating protocols: (FFPE) blocks used to cut 4 μm sections onto glass slides. DARC/ACKR1 staining was done using a goat anti-human polyclonal antibody (Novus Biologicals, NB100-2421, Isotype IgG). CCL2 and CXCL8 staining were both done using mouse anti-human monoclonal antibodies (R&D Systems, MAB2791, Isotype IgG2B and Lifespan Biosciences, LS-B6427, Isotype IgG1, respectively).

Statistics.

Statistical analyses were done using appropriate functions in JMP (SAS) Pro v. 13.0.0. All student's t-test performed were two-tailed and the appropriate absolute p-values are indicated in the figure legends of each statistical analysis. F values are reported for ANOVA analyses and p-values are reported for linear regression or paired t-test analyses. Numbers of included data points and degrees of freedom are also shown for the appropriate analyses.

Results

DARC/ACKR1 Tumor Expression is Significantly Different Across Race Groups and Tumor Molecular Subtypes.

Figure 4:
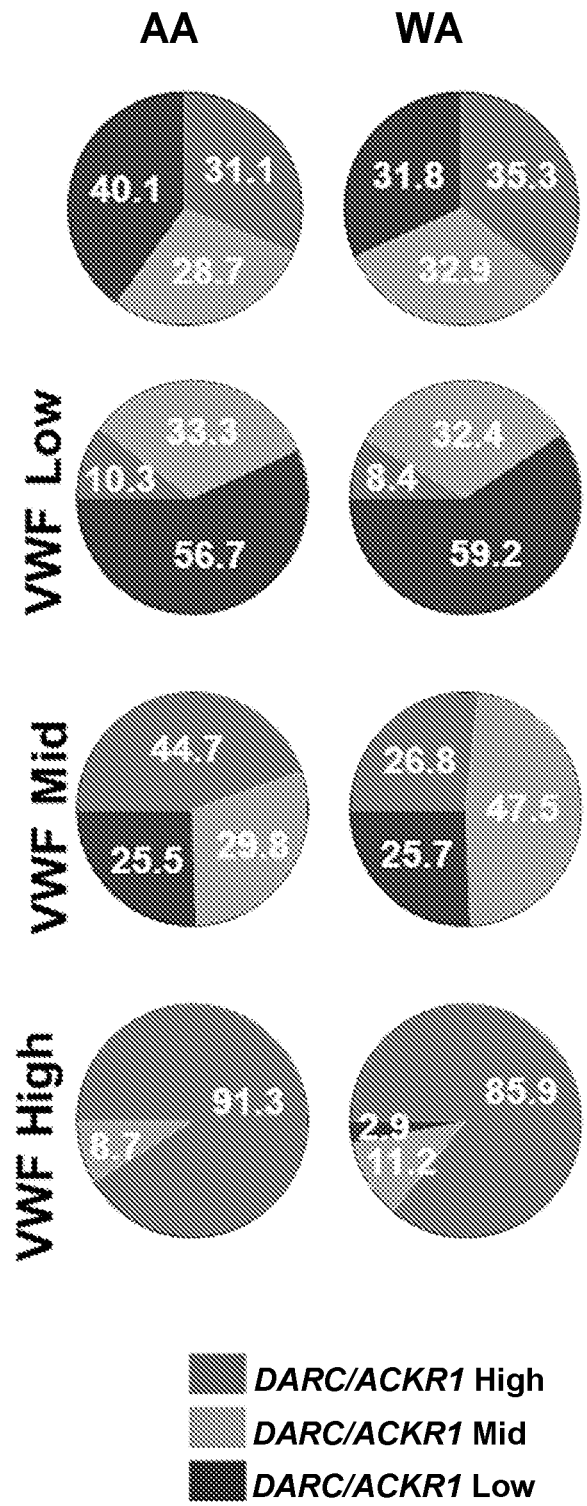
FIG. 4. DARC/ACKR1 is significantly associated with VWF, breast cancer molecular subtypes, and pro-inflammatory chemokines in TCGA data. TCGA Breast Cancer RNAseq data (n=838) was used to compare (A, top) the distribution of DARC/ACKR1 expression subgroups (high, n=289; medium, n=268; low, n=281) and race (African- Americans, n=167, AA; White Americans, n=671, WA). (A, bottom) same as (A, top) but with VWF expression subgroups (VWF Low, n=336; VWF Mid, n=309; VWF High, n=193, p=0.06, ANOVA) by race. (B, top) Distribution of DARC/ACKR1 expression subgroups compared to molecular breast cancer subtypes (Basal-like, n=74; HER2+, n=24; Luminal A, n=196; Luminal B, n=58, p<0.0001). (B, bottom) same as (B, top) but broken down by race. (C) Heat map (UCSC Xena Browser) of TCGA breast invasive carcinoma RNAseq gene expression data (IlluminaHiSeq) shows cytokine expression after creating dichotomized DARC/ACKR1 positive (high) and negative (low) subgroups. Gene expression was assessed in 399 breast tumors against a panel of 67 genes associated with known cytokines showing low expression, and high expression. Welch's t-test was performed on CCL2 (p=0.0000, t=10.28) and CXCL8 (p=0.0003, t=−3.644). (D) DARC/ACKR1 high and low categories compared to CCL2 (left, student's t-test, p<0.0001, DF=438.05) and CXCL8 (right, student's t-test, p<0.0001, DF=376.25) gene expression (mean±SEM).
Figure 4:
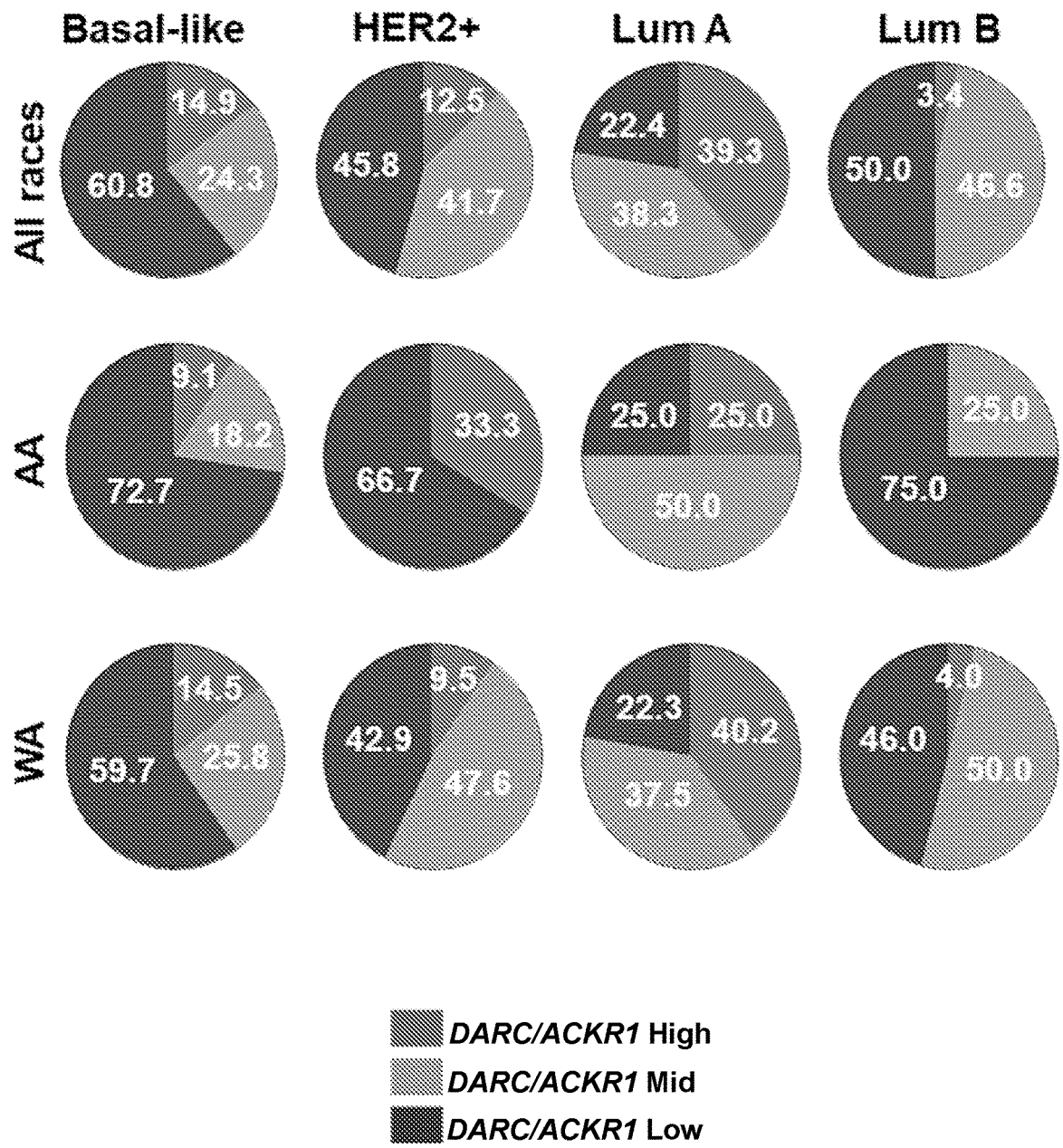
Figure 4:
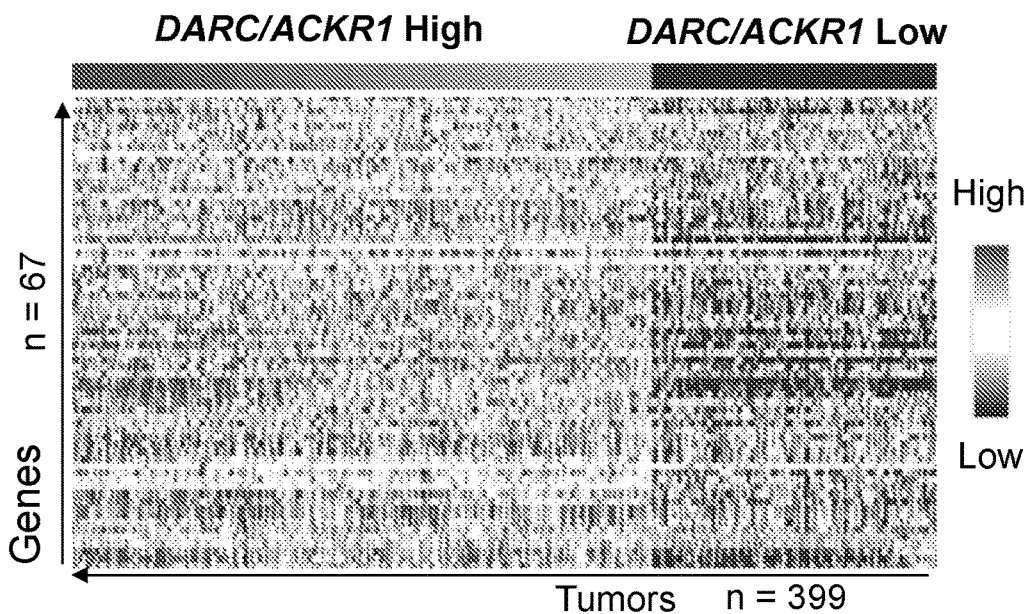
Figure 4:
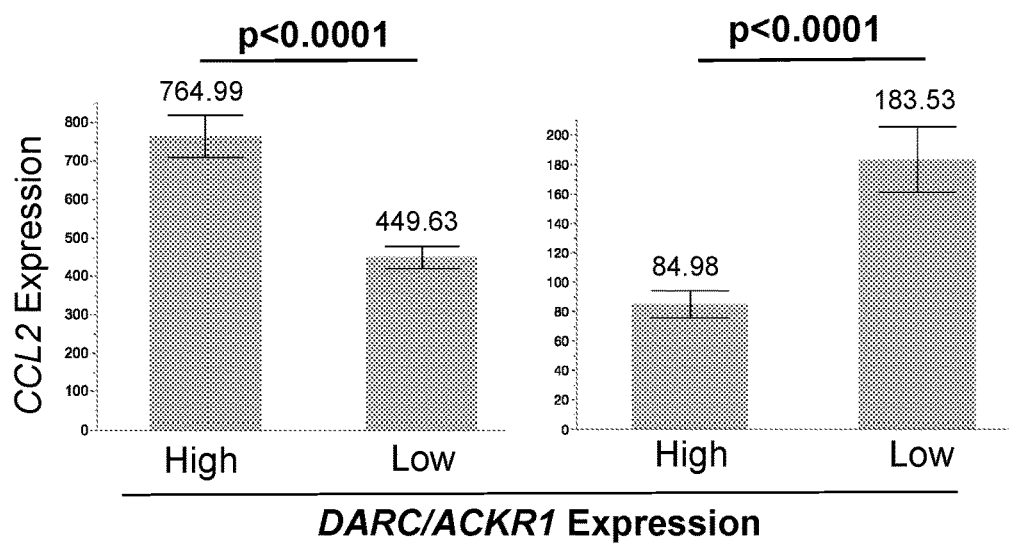

In this disclosure we investigated DARC/ACKR1 expression differences at a high resolution, using the TCGA breast infiltrating carcinoma (BrC) RNAseq dataset (n=838; 167 AAs, 671 WA), and found a broad range and distribution of DARC/ACKR1 expression across the cohort (FIG. 1A-B). A statistical response screen across anthropomorphic and clinical variables suggested that DARC/ACKR1 tumor expression was distinct across race and tumor phenotypes (FIGS. 1 C and D). Our analysis revealed that WA have a nearly equal distribution of DARC/ACKR1 tumor expression subgroups, with the highest proportion being DARC/ACKR1-high (35.3%), AAs have the highest proportion of DARC/ACKR1-low tumors (40.1%) (FIG. 4A, top). These race-related trends indicate a distinct regulation of DARC/ACKR1 that is likely linked to geographic genetic ancestry, which is closely associated with race.

However, because DARC/ACKR1 expression occurs across all organ systems within endothelial cells of post-capillary venules, we also considered the relative expression of an endothelial cell-type marker, Von-Wilderbrand Factor (VWF) within the tumor samples. When tumors were stratified by DARC/ACKR1 status and VWF (FIG. 4A, bottom), the differences of DARC/ACKR1 status between race groups were more evident (p=0.06), just above the threshold for significance. Interestingly, the correlation of DARC/ACKR1 to VWF was very significant (p<0.0001, FIG. 1F), which suggests that a significant portion of DARC expression within these tumor samples might be derived from endothelial tissue. However, even within tumors with low VWF, we still find high expression of DARC/ACKR1, particularly in WA patients.

In the context of current standards of breast tumor molecular phenotypes, we also found that DARC/ACKR1 tumor status (e.g. DARC-high vs DARC-low) was significantly distinct across the PAM50 subtype categories (p<0.0001), as defined by RNAseq gene expression profiles (FIG. 4B, top). Specifically, nearly 40% of the PAM50 Luminal A subtypes are DARC/ACKR1-high tumors, which is the largest proportion of DARC/ACKR1-high tumors across all subtypes. Contrarily, the highest proportion of DARC/ACKR1-low tumors are within the Basal-like subtype, making up over 60% of this category. When the PAM50 subtypes are also stratified for self-reported race (FIG. 4B, bottom), we observed clear distinctions in the distributions of DARC/ACKR1 tumor status between AA and WA, though these differences did not pass thresholds for statistical significance.

Figure 5:
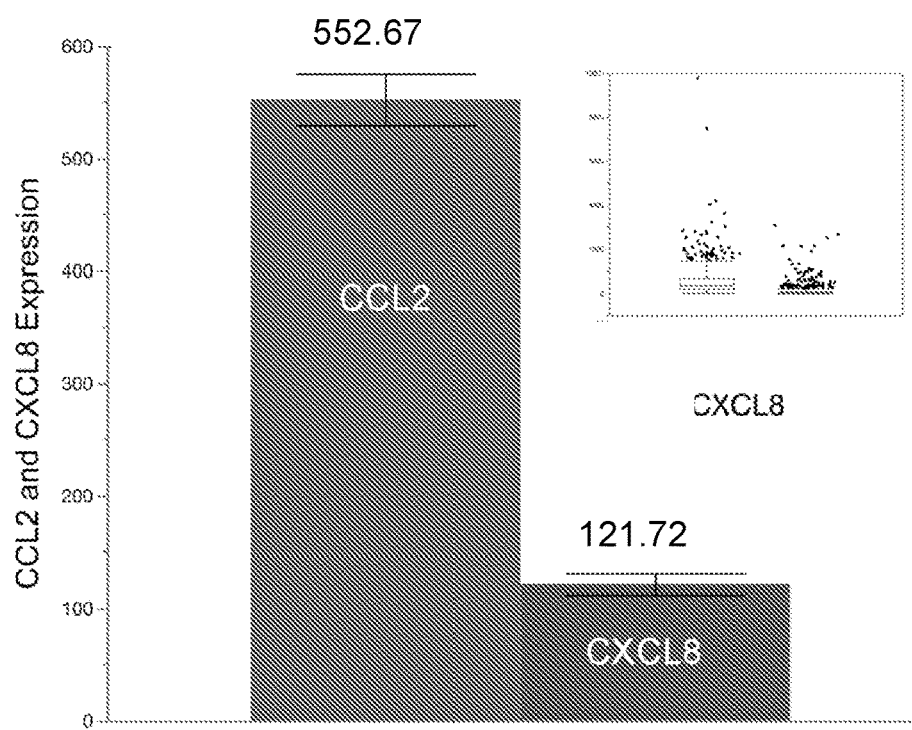
FIG. 5. Distribution and chemokine correlations in TCGA data. (A) Mean CCL2 (blue, AA, mean=552.67, SEM=45.87; WA, mean=544.61, SEM 26.45) and CXCL8 (red, AA, mean=119.34, SEM=16.43; WA, mean=122.31, SEM=11.30) expression by race. (C) Linear regression showing positive correlation between DARC/ACKR1 and CCL2 mean expression (p<0.0001, $R^2$=0.08). (D) Linear regression showing negative correlation between DARC/ACKR1 and CXCL8 mean expression (p=0.0140, $R^2$=0.007).
Figure 5:
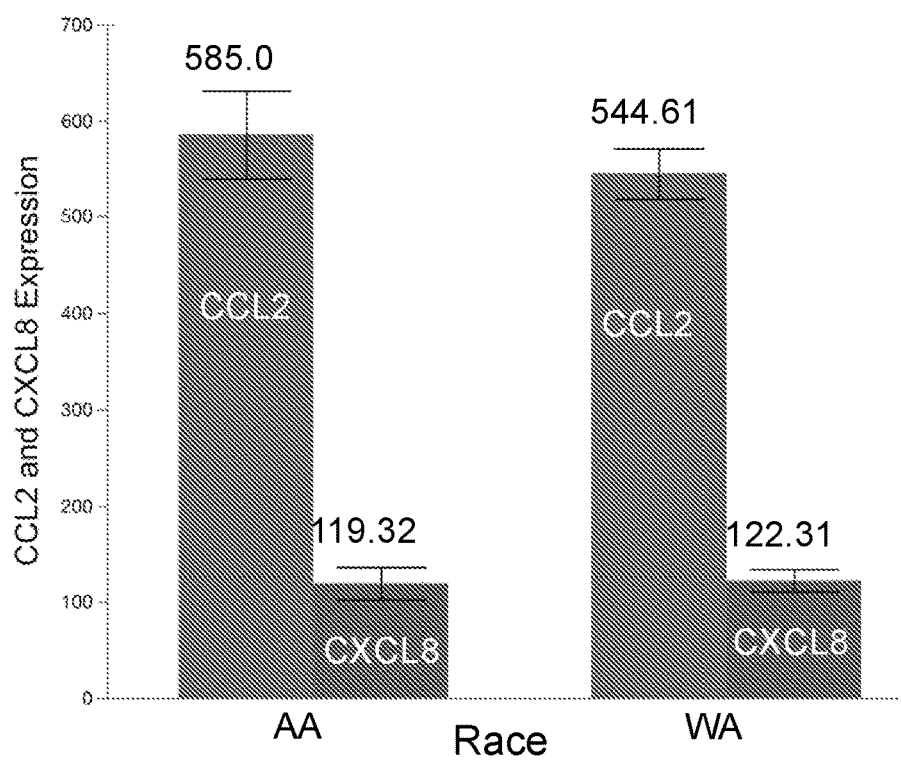
Figure 5:
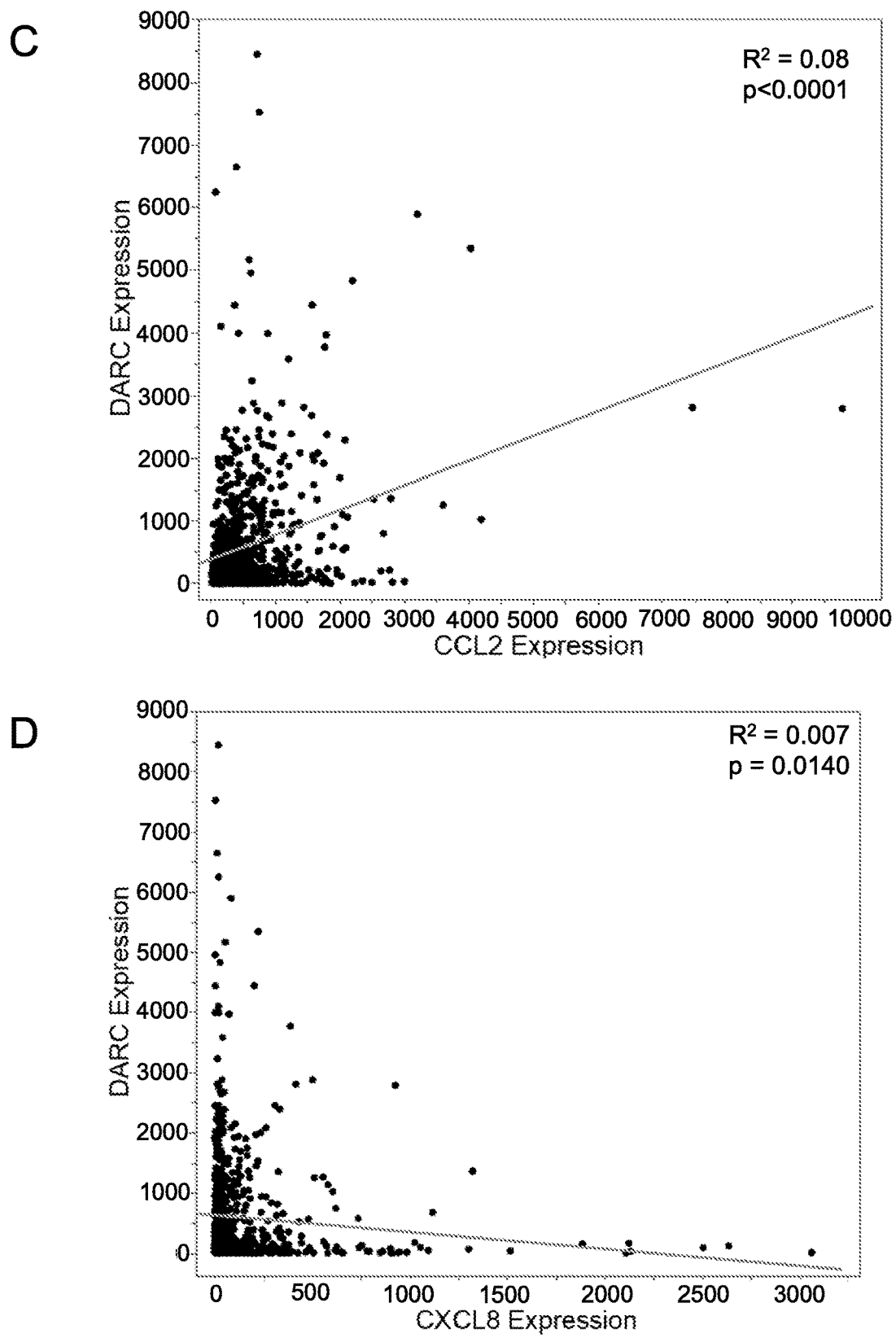

To investigate whether status of DARC/ACKR1 tumor expression is connected to genes that function in DARC/ACKR1-related chemokine signaling pathways, we investigated over 60 chemokine genes (Table 1) and found that there were significant differences in chemokine gene expression, correlated with DARC/ACKR1 status (FIG. 4C, Table 2). Two of these genes, CCL2 and CXCL8, are high-affinity DARC/ACKR1 binding targets and have significant expression in breast tumors (FIG. 5A) correlated with DARC/ACKR1 expression (FIGS. 5 C and D). When compared across DARC/ACKR1 tumor types, we found that DARC/ACKR1-high tumors have significantly correlated high levels of CCL2 ($p<0.0001$) but significantly anti-correlated lower levels of CXCL8 in primary tumors ($p<0.0001$, FIG. 4D).

Circulating Levels of DARC/ACKR1-Related Chemokines, CCL2 and CXCL8, are Associated with Disease Status, Duffy-Null Phenotype, Self-Reported Race and African Ancestry-Specific Alleles of DARC/ACKR1.

We conducted a Luminex analysis in an independent breast cancer case-control cohort (case, n=266, controls, n=156) to identify associations among DARC/ACKR1-related chemokines and histopathological variables in our cohort. When comparing race between cases and controls overall, we identified a significant difference in circulating CCL2 levels between AA cases and WA cases, where AA had significantly lower CCL2 than WA ($p=0.0031$, FIG. 6A, top). We did not observe a significant difference between cases and controls in AA, but CCL2 levels were decreased in AA cases only, a trend we did not observe in WA. We also observed a significant increase in circulating CXCL8 levels in AA cases ($p=0.0013$, FIG. 6A, bottom) and WA cases ($p<0.0001$, FIG. 6A, bottom) compared to their respective controls. These lower circulating CCL2 protein expression levels in AAs compared to WAs is a trend that indicates a potential race-specific circulatory inflammatory response, however this same trend was not observed in the tumor gene expression data from TCGA (FIG. 5B).

Figure 6:
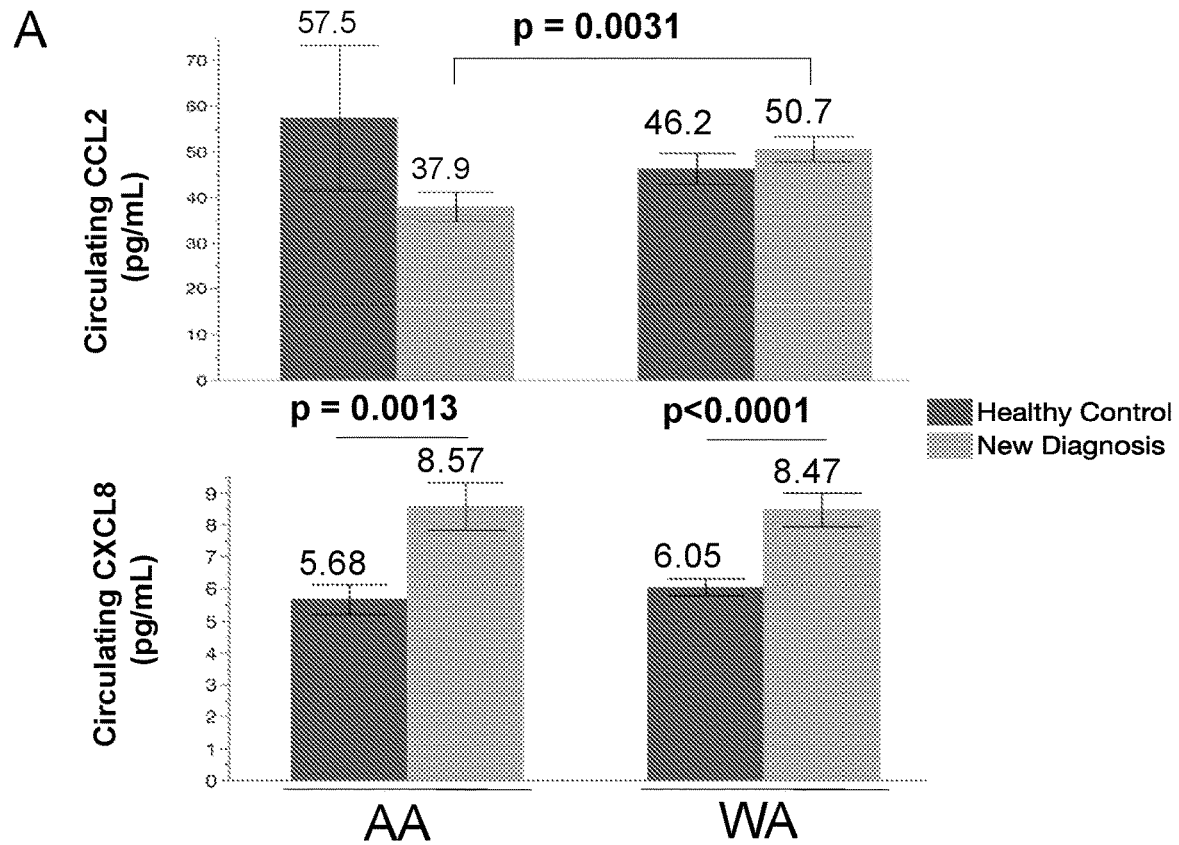
FIG. 6. DARC/ACKR1 phenotype and genotype associated with race and pro-inflammatory chemokines in case-control cohort (n=422). (A) Case-control comparison of circulating CCL2 (top) and CXCL8 (bottom) levels by race (student's t-test, p=0.0031, DF=182.09). (B) Representative images of DARC/ACKR1 phenotyping on RBCs; BF=bright field, DARC/ACKR1=middle row, plasma membrane control=bottom row, scale=50 m. (C) Distribution of DARC/ACKR1 phenotype (top, positive=black, intermediate=dark grey, negative=light grey, n (AA)=71, n (WA)=186) and genotype (bottom, rs2814778; AA=black, homozygous reference; AG=dark grey, heterozygous; GG=light grey, homozygous alternate, n (AA)=101, n (WA)=262) compared to race. (D) DARC/ACKR1 phenotype on RBCs compared to circulating CCL2 (left, student's t-test, p=0.0436, DF=42.88) and CXCL8 levels (right); Inter.=intermediate. (E) Same as (D) but with DARC/ACKR1 genotype (rs2814778; CCL2, left, ANOVA, F=0.0002, DF=212, student's t-test, p<0.0001, DF=137.31, student's t-test, p=0.0176, DF=27.47, CXCL8, right).
Figure 6:
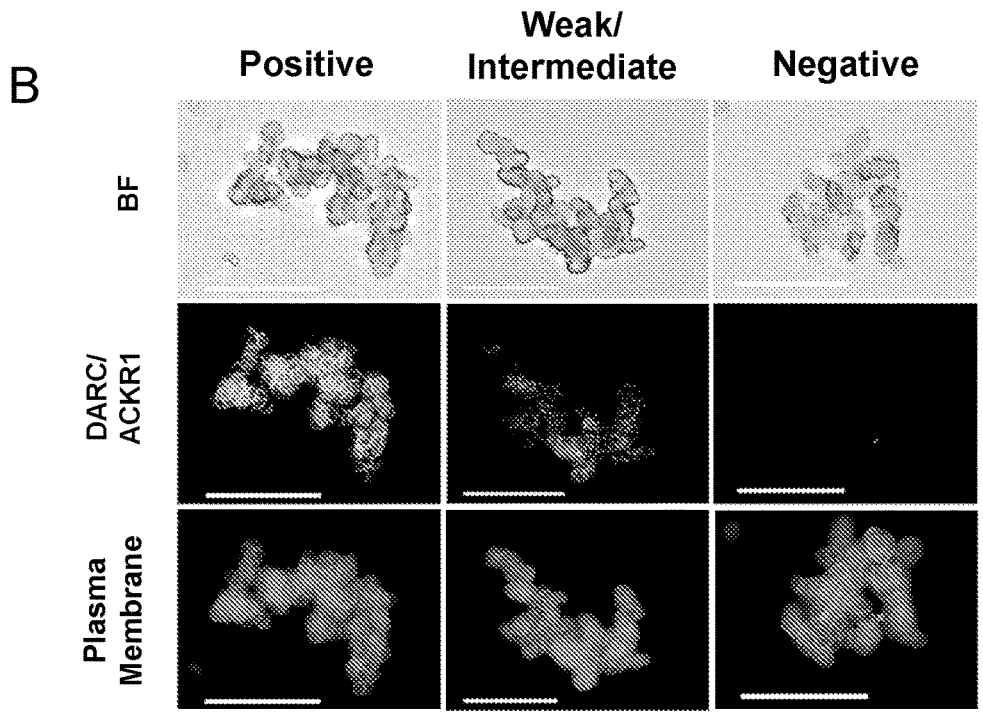
Figure 6:
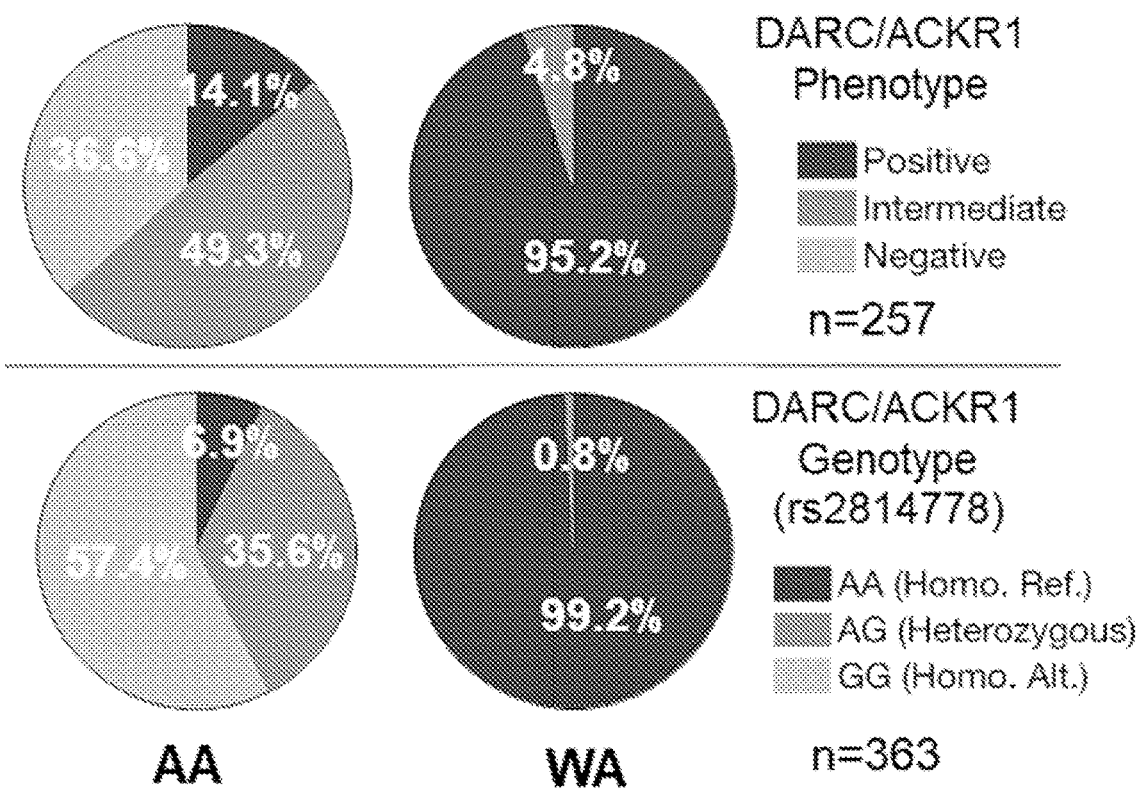
Figure 6:
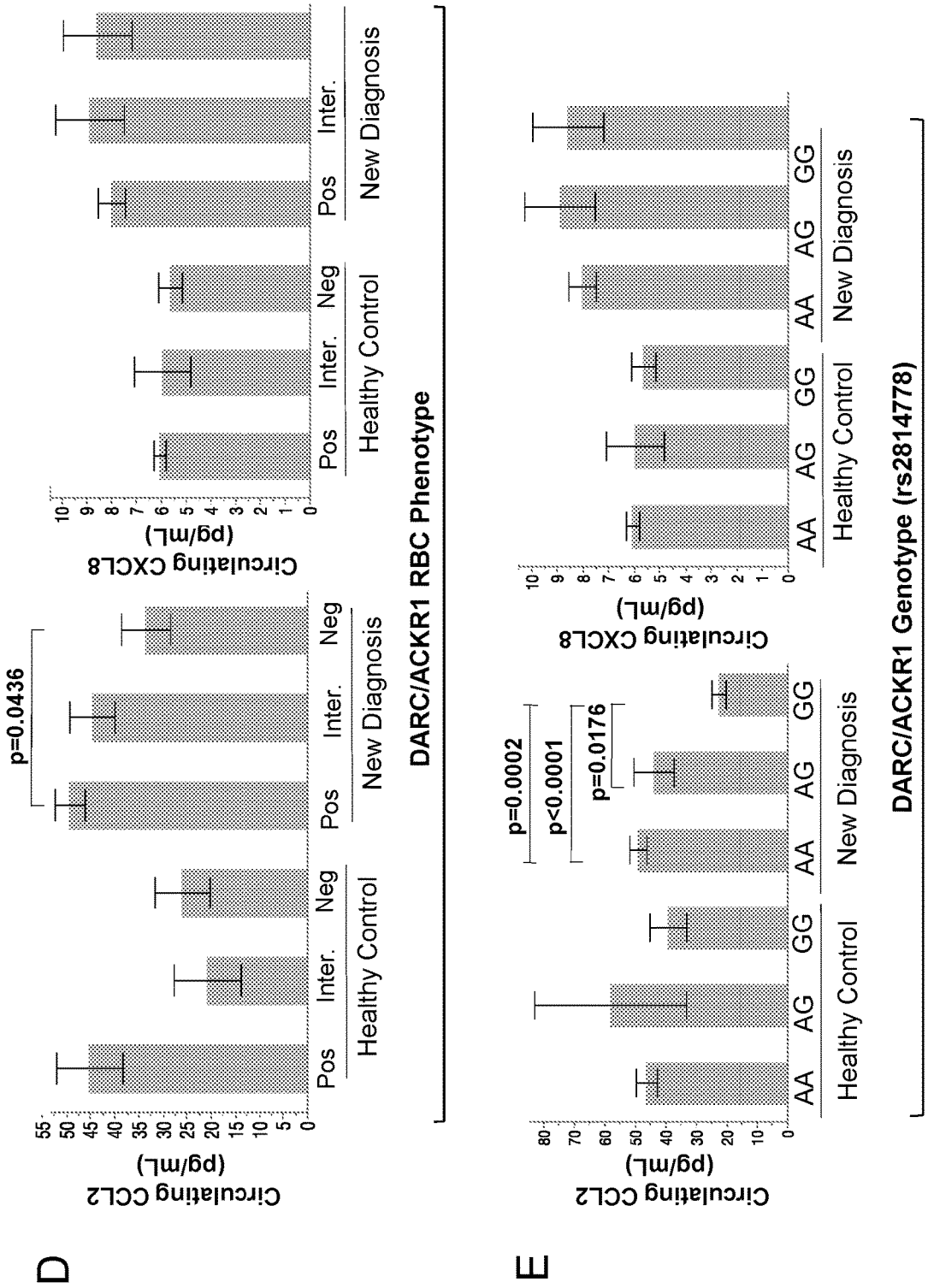

To determine the distribution and impact of the Duffy-null phenotype on cancer-related inflammatory response in our cohort, we tested our cases and controls for the erythrocyte-silent phenotype (FIG. 6B), as well as the Duffy-null gene mutation (rs2814778). As expected, we found both a higher frequency of the DARC/ACKR1$^{es}$/Duffy-null blood group and the Duffy-null/ACKR1$^{es}$ allele (rs2814778) frequency in AAs (FIG. 6C). These distributions were in concordance with published global and population-specific allele frequencies (Table 4). We then compared circulating levels of CCL2 and CXCL8 with the DARC/ACKR1 RBC phenotype and Duffy-null genotype for case and control groups (FIG. 6D-E). For phenotype, we found significant differences in CCL2 levels between those with positive DARC/ACKR1 erythrocytic expression and negative expression among the newly diagnosed breast cancer cases only ($p=0.0436$, FIG. 6D, left). When considering genotype, we found significant differences in CCL2 levels across all newly diagnosed cases ($p=0.0002$, FIG. 6E, left). We also observed individual associations between those that are homozygous for the reference allele (AA) and homozygous for the alternate Duffy-null allele (GG, $p<0.0001$, FIG. 6E, left), and those that are heterozygous and homozygous for the Duffy-null allele ($p=0.0176$, FIG. 6E, left) in newly diagnosed cases.

Figure 7:
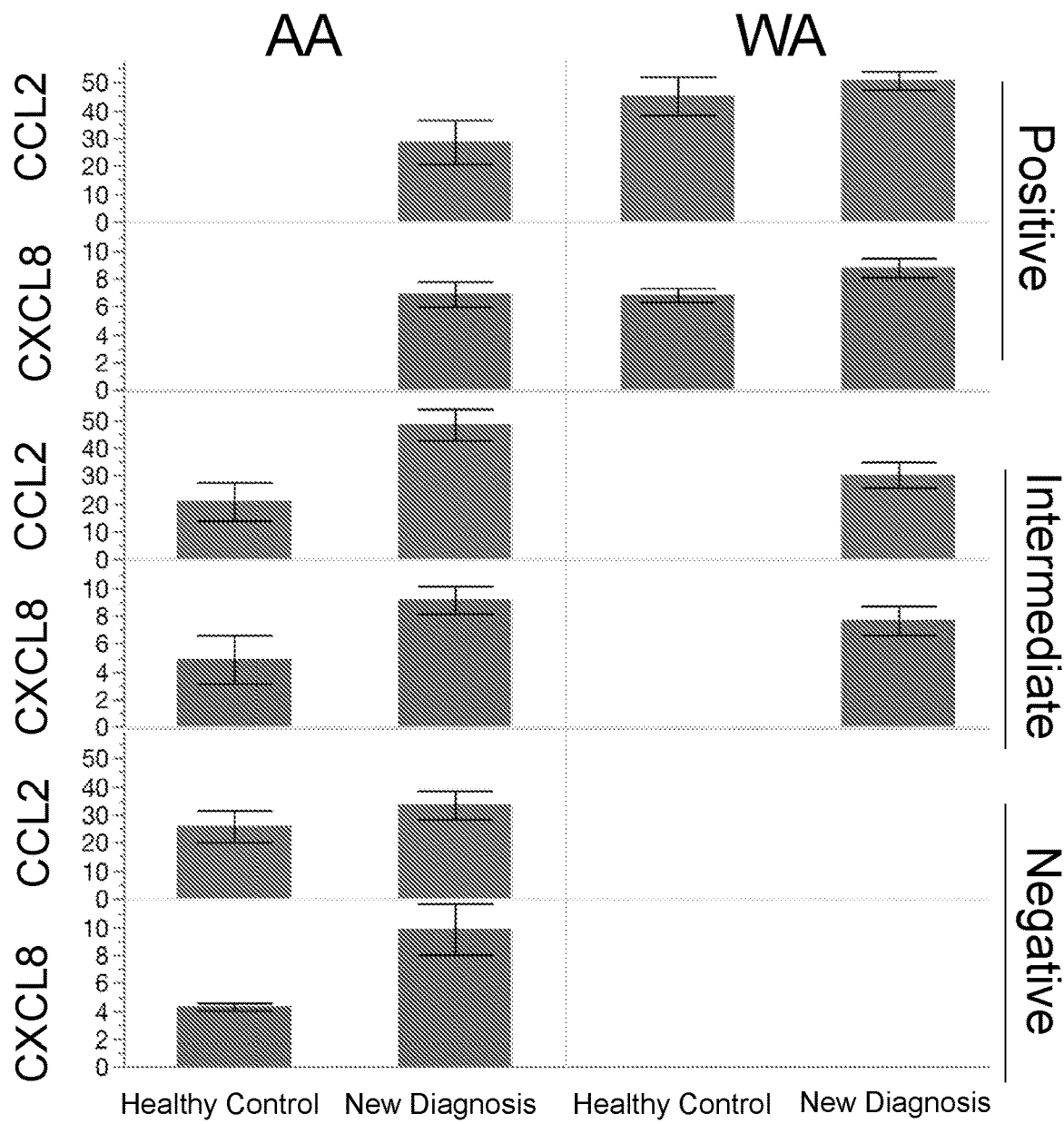
FIG. 7. Associations between race and phenotype in case-control cohort. Mean circulating CCL2 and CXCL8 concentrations by race, patient status and DARC/ACKR1 RBC phenotyping.

This correlation was similar when the phenotype groups were broken down by race (FIG. 7). Interestingly, the significant differences in CCL2 circulating levels increased among the DARC/ACKR1 allele carriers (FIG. 6E) indicating that the genetic allele is a more robust indicator of these circulating chemokine levels than the RBC phenotype, in newly diagnosed patients.

DARC/ACKR1 Tumor Gene Expression is Associated with Distinct Tumor-Associated Leukocyte Gene Expression Profiles.

Figure 8:
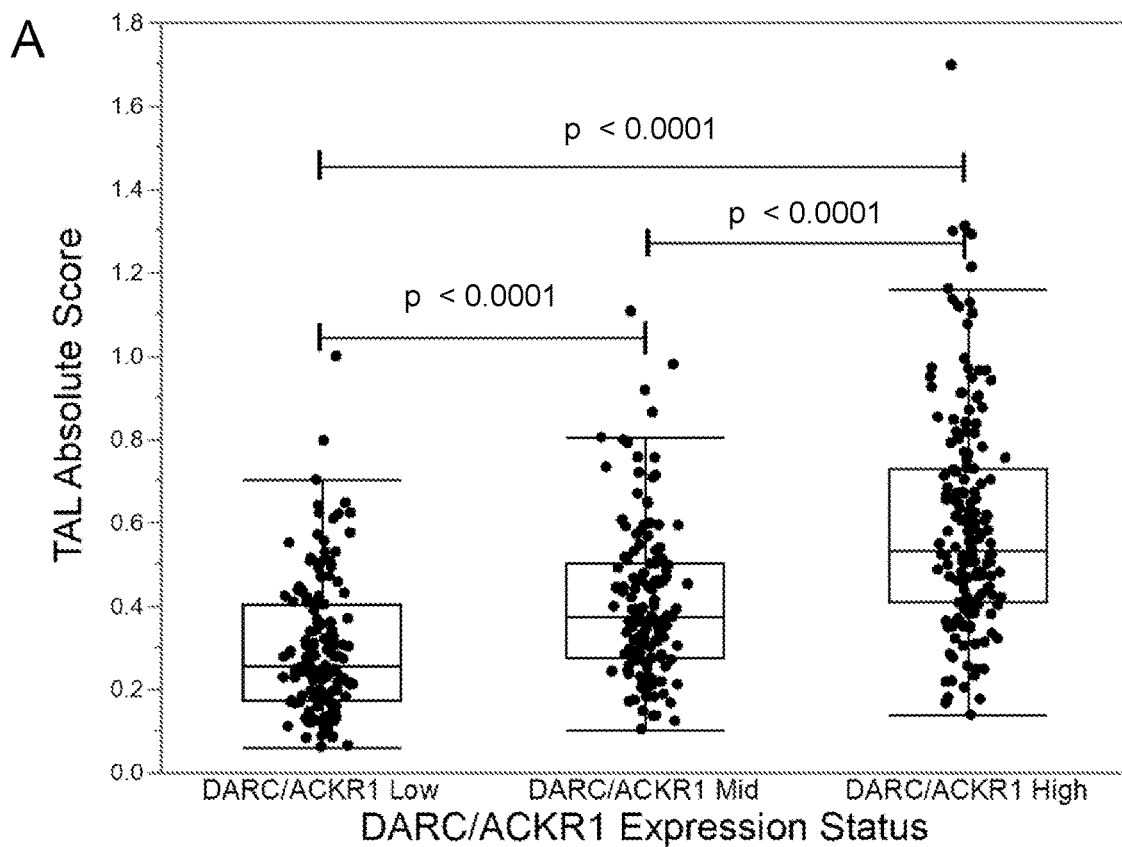
FIG. 8. DARC/ACKR1 expression levels are positively and significantly associated with TAL abundance in breast tumors. Using CIBERSORT absolute mode, the absolute score totals the quantitative abundance of each individual leukocyte population among TCGA breast primary cases. Those cases with significant CIBERSORT results (p<0.05) were included in this analysis (n=472). (A) The total TAL absolute score reported is a total of abundance scores across all 22 tumor-associated leukocyte populations. By plotting total TAL absolute score by DARC/ACKR1 expression status, we see significant increases in TAL abundance as DARC/ACKR1 expression is increasing between low, medium and high categories. (B) Looking at individual TAL populations, panel B shows the 12 leukocyte populations that are significantly different between DARC/ACKR1 expression levels. Student's t-test was performed comparing each DARC/ACKR1 expression group, and the p-values are shown in panel (C).
Figure 8:
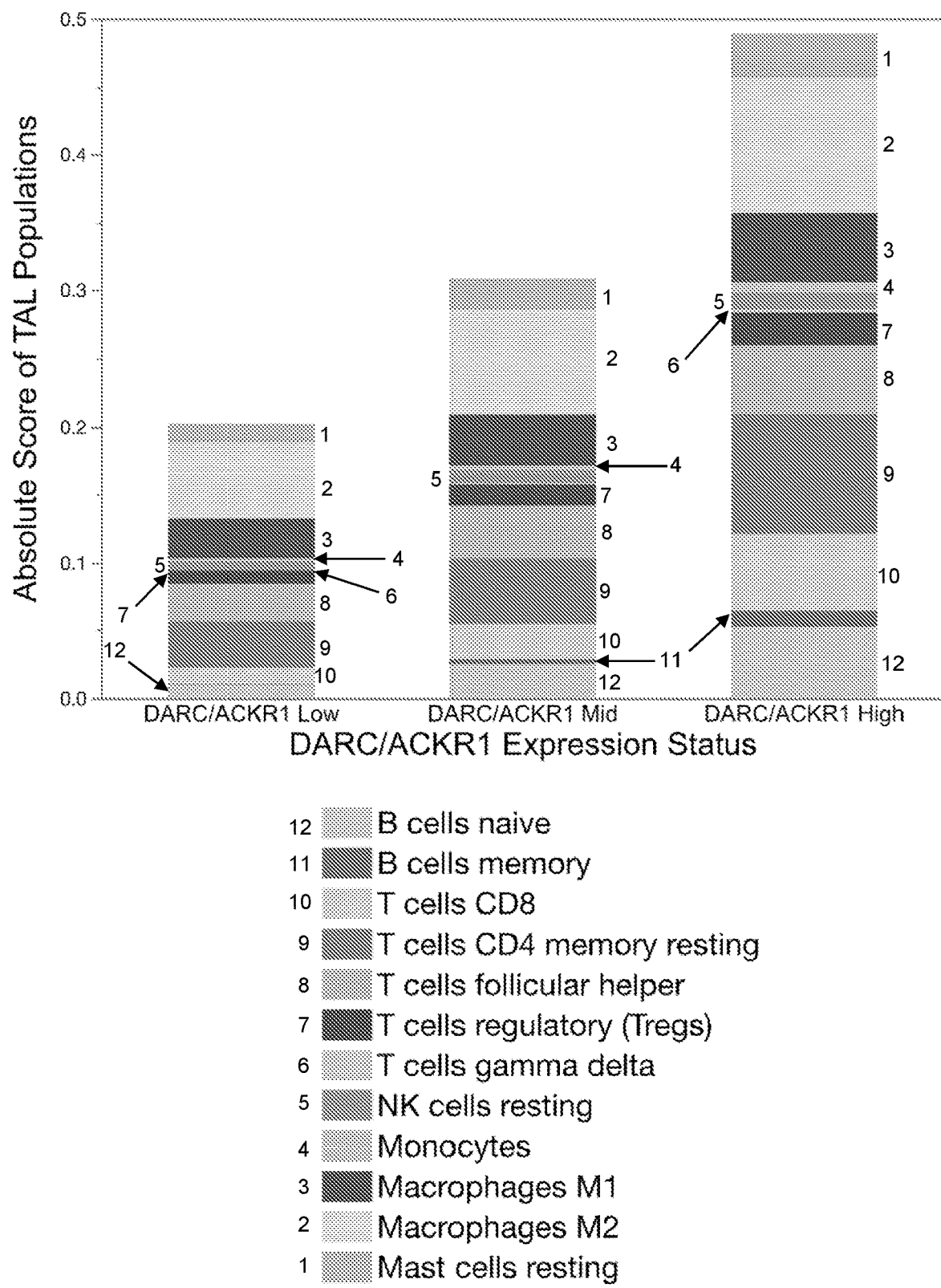

Because the chemokines under regulation of DARC/ACKR1 direct the infiltration of immune cells during inflammatory responses, we investigated the differences in immune cell responses, relative to DARC/ACKR1 tumor expression. Using TCGA RNA-seq data, we employed a cell type deconvolution algorithm, CIBERSORT, and determined that overall leukocyte infiltration (Total TAL score) is greater in DARC/ACKR1-high tumors (FIG. 8A). These counts were directly correlated with quantified DARC/ACKR1 gene expression (FIG. 9A), suggesting that DARC/ACKR1 could be a marker that predicts the level of tumor immunogenicity. The increase of total immune cell infiltrates was also correlated with increasing CCL2, but to a lesser extent (FIG. 9B), indicating that CCL2 has some influence on, but is not sufficient for, the total observed immune cell profiles.

Figure 9:
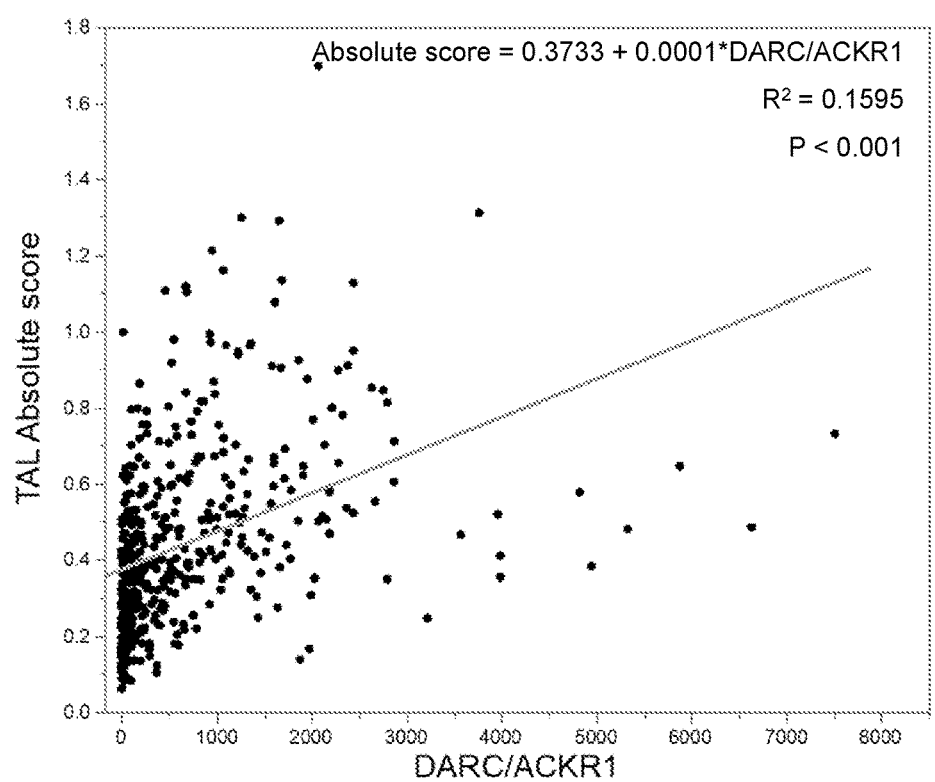
FIG. 9. DARC/ACKR1 and CCL2 expression are positively and significantly associated with Total Absolute TAL scores. Scatterplots showing the positive correlation between (A) DARC/ACKR1 expression and (B) CCL2 expression with total TAL absolute scores. Fit line equations, $R^2$ values, and the p-values of the associations are reported in the plots. (C) Distribution of TAL populations across DARC/ACKR1 status by race.
Figure 9:
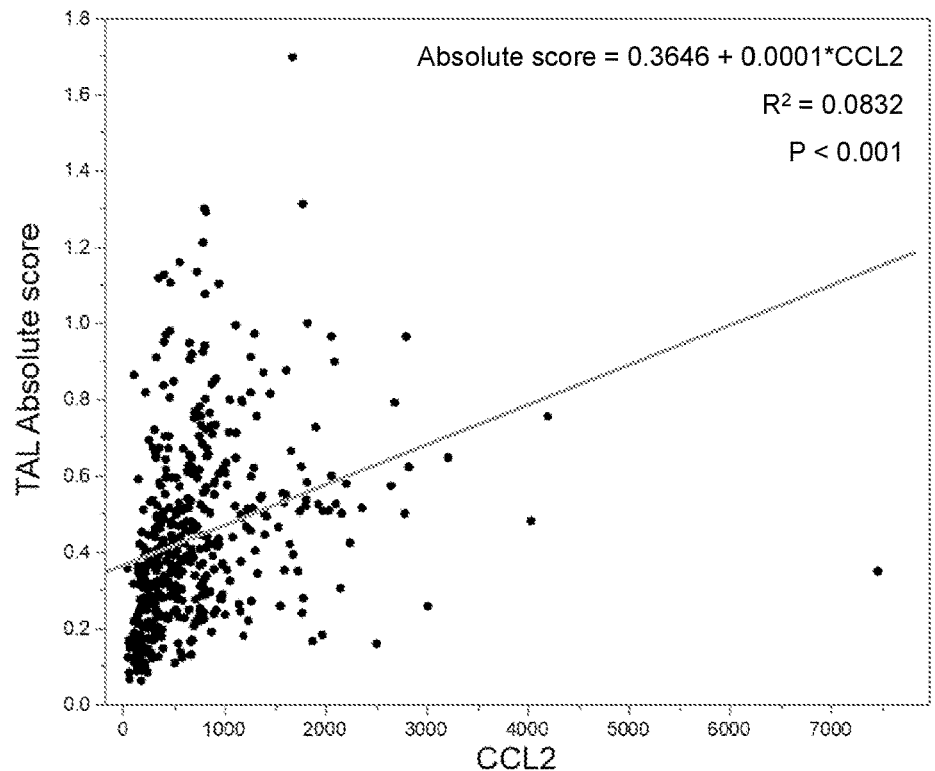
Figure 9:
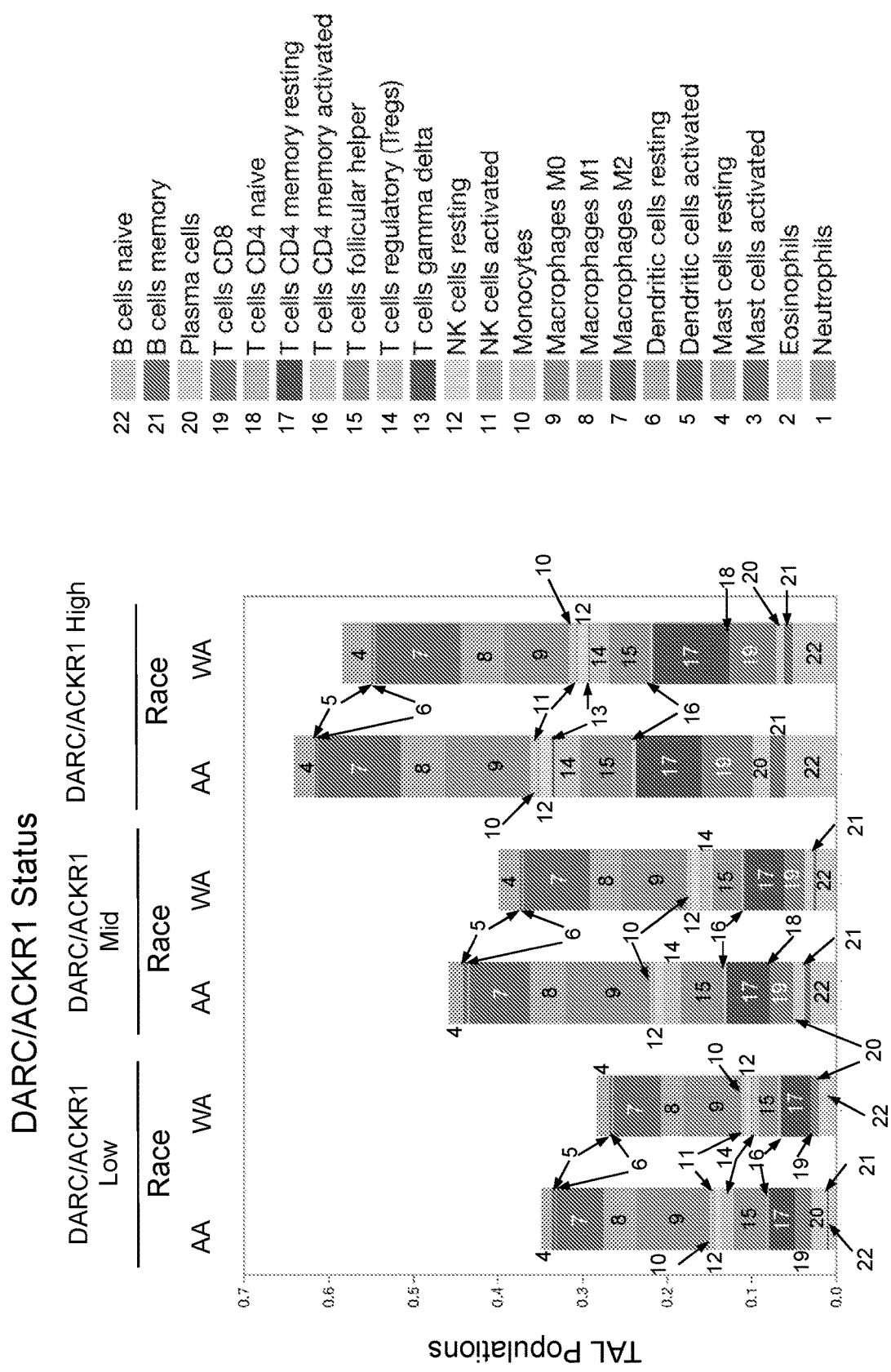
Figure 10:
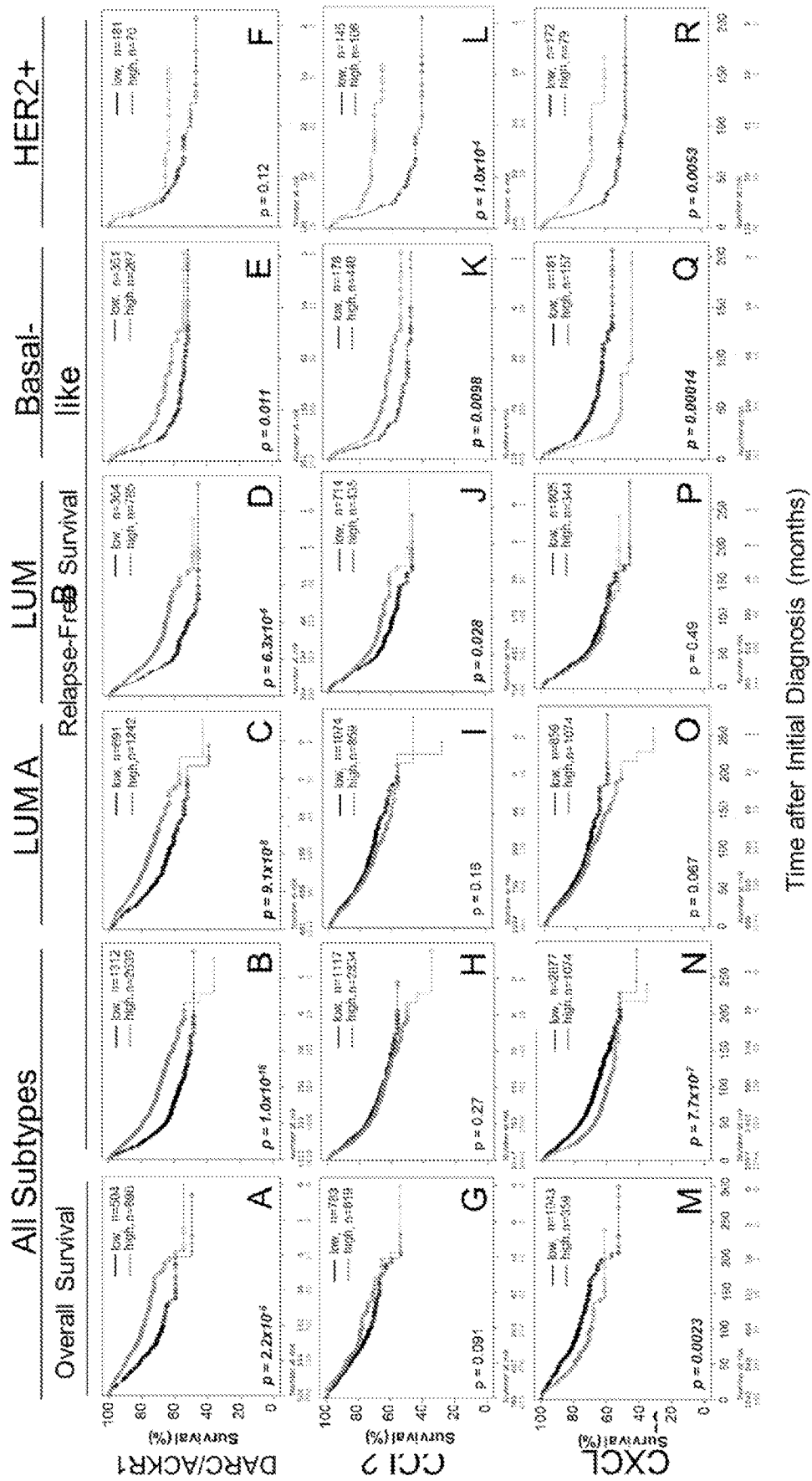
FIG. 10. High DARC/ACKR1 tumor expression is associated with significantly higher survival in breast cancer. Kaplan-Meier (KM) survival curves (www.kmplot.com) of breast cancer patients dichotomized into DARC/ACKR1 (208335_s_at, top row), CCL2 (216598_s_at, middle row), and CXCL8 (211506_s_at, bottom row) low (black) and high (grey) categories showing overall survival (A, G, M) and relapse-free survival (B-F, H-L, N-R) by all molecular subtypes and four individual subtypes (Lum A=Luminal A, Lum B=Luminal B, Basal-like, and HER2+=Human Epidermal Growth Factor Receptor 2).

We found distinctions in both the proportions and combinations of specific infiltrating immune cell subtypes of DARC/ACKR1-high tumors compared to DARC/ACKR1-low tumors. Specifically, there is an increase in numbers of B cells, T cells (CD8 and CD4), T-regulatory cells and activated macrophages (M1 and M2) (FIGS. 8B and C). Conversely, DARC/ACKR1-low tumors appear to lack dendritic and B memory cells. Differences in the DARC/ACKR1-associated immune cell type profiles are also present among race groups, ($p=0.08$). Specifically, AA patients with the DARC/ACKR1-low tumor subtype have more infiltrating M0 macrophages and fewer B cells compared to WA patients (FIG. 9C).

Higher DARC/ACKR1 Tumor Gene Expression is Associated with Longer Survival.

To determine the clinical significance of DARC/ACKR1 gene expression in breast tumors, we investigated publicly available datasets for associations of DARC/ACKR1 tumor gene expression with survival (cohorts are summarized in Table 6). We found that when patients have higher DARC/ACKR1 tumor expression, they have significantly longer OS and RFS (FIG. 10A-B) (OS $p<2.2\times10^{-6}$, n=1,402; RFS $p<1\times10^{-16}$, n=3951). This survival association remained significant for RFS across all molecular subtypes (including; Luminal A, Luminal B, Basal-like), with one exception, HER2+(FIG. 10A-E). Similarly, the <5-year survival outcome in TCGA is also linked to DARC/ACKR1 tumor expression (FIG. 1G). The impact of CCL2 (FIG. 10G-L) and CXCL8 (FIG. 10M-R) can also be seen within certain molecular subtypes of breast cancer, but often to a lesser degree than DARC/ACKR1 associations. In all subtypes, it is clear that inflammatory markers related to DARC/ACKR1 tumor expression have a significant impact on survival. Specifically, CCL2 has the most significant survival impact on basal-like and HER2+ cases (FIGS. 10K and L) where higher CCL2 is associated with longer survival. Contrarily, CXCL8 also has a significant impact in basal-like cases (FIG. 10Q) but in the opposite direction, where low expression of CXCL8 leads to longer survival. This opposing trend of CCL2 and CXCL8 is directly associated with DARC/ACKR1 status, as shown previously in FIG. 4D.

In Tumor Epithelial Cells, DARC/ACKR1 is Correlated with Higher CCL2 and Lower CXCL8 by Immunohistochemistry Data.

Figure 11:
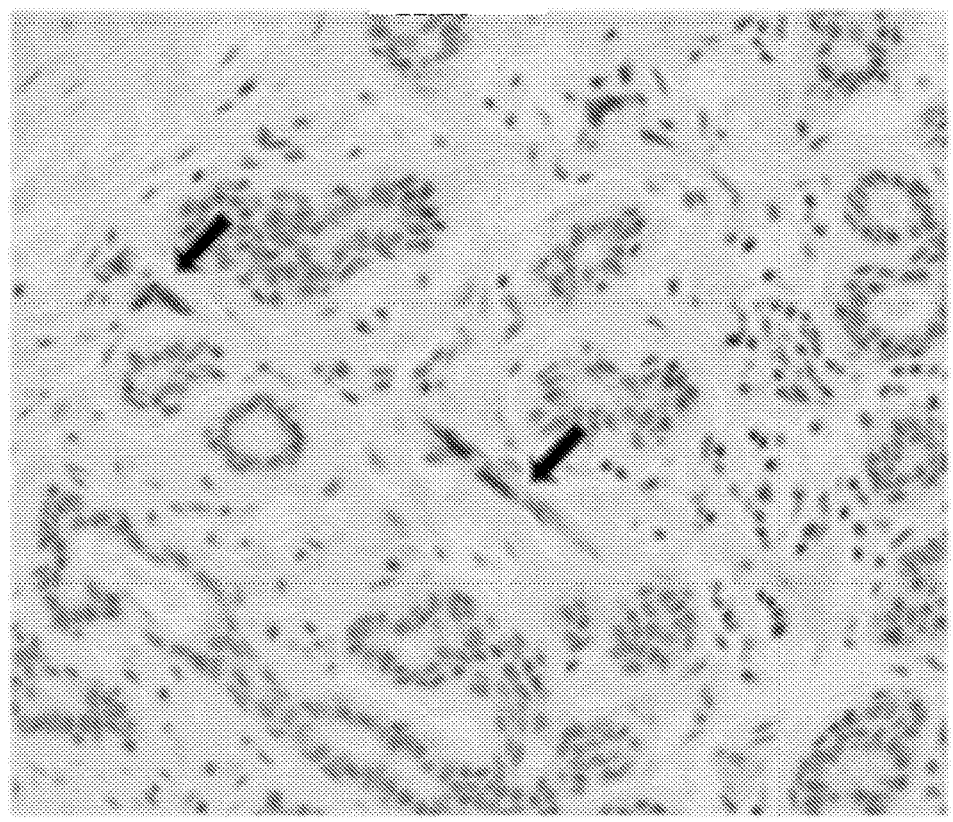
FIG. 11. (A) Normal breast tissue with positive DARC/ACKR1 staining on endothelial tissue only. (B) DARC/ACKR1 positive epithelial staining in normal ductal (CRL 8799) and TNBC (HCC 1806) cell lines.
Figure 11:
Figure 12:
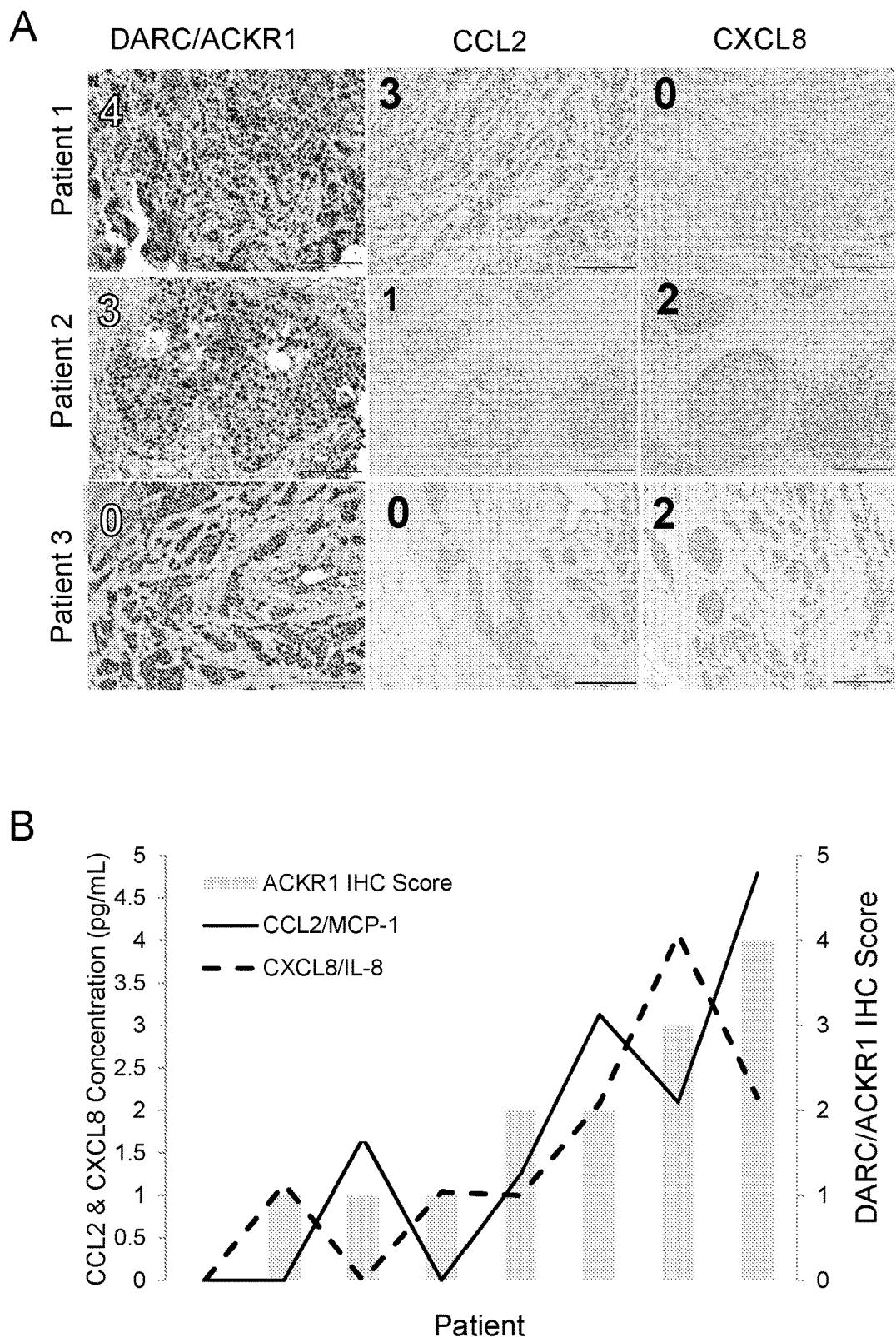
FIG. 12. DARC/ACKR1 may correlate with pro-inflammatory chemokines in breast tumor tissue. (A) Primary breast tumors stained for DARC/ACKR1 (left column), CCL2 (center column), and CXCL8 (right column) by IHC and scored on a numerical system of 0-4, bar=200 µm. (B) Linear correlation between DARC/ACKR1 IHC scores (grey bars) and circulating CCL2 (straight line) and CXCL8 (dotted line) concentrations from Luminex assay (n=8).

DARC/ACKR1 has been shown to be expressed on endothelial post-capillary venules, which are present in normal breast tissue (FIG. 11A) and tumors as well. However, our data in breast cell lines indicated DARC/ACKR1 was expressed in tumor cells (FIG. 11B). To confirm the genomic and cell line data, we conducted IHC on a small cohort of primary tumor specimens (n=8) to validate the spatial expression of DARC/ACKR1 in the tumor microenvironment. Our initial results indicate that when DARC/ACKR1 is expressed, it was not limited to endothelial cells but was uniformly expressed within the tumor-specific epithelial cells. This finding validates the VWF-associated DARC expression trends show in FIG. 4A and FIG. 1F. Specifically, IHC subset suggests that the DARC/ACKR1 gene product is also expressed over the full spectrum of scoring (0-4) in our cohort (FIG. 12A), similar to the RNA-seq distributions (FIGS. 1A and B). Also, like the RNAseq findings, tumors with high DARC/ACKR1 IHC scores showed correlated high CCL2 expression and low CXCL8 expression (FIG. 12A), although these associations were observed in a very small IHC cohort (n=8)

Considering that the role of DARC/ACKR1 on epithelial cells would be similar to that on endothelial cells, we investigated whether circulating chemokine levels were associated with DARC/ACKR1 tumor scores. We integrated the Luminex chemokine assays from our clinical cohort with a pilot IHC study with a subset of cases and found a significant positive correlation between DARC/ACKR1 tumor scores and circulating levels of CCL2 (p=0.0061) and CXCL8 (p=0.0291) (FIG. 5B and Table 3). This finding was also aligned with our RNAseq findings for CCL2, CXCL8 and DARC/ACKR1 levels.

In this disclosure, we have shown that a west African-specific allele of DARC/ACKR1, a gene that regulates immune and inflammatory response, is strongly associated with both the epithelial expression and circulating levels of CCL2 and CXCL8, which are pro-inflammatory chemokines previously shown to be related to cancer progression. We have thusly implicated the epithelial tumor expression of DARC/ACKR1 to be a key modulating factor of chemokines in tumors, confirmed in small IHC study within our clinical cohort. These findings indicate that DARC/ACKR1 has a dual role in controlling chemokine gradients that determine tumor immune cell response, specifically by regulating both the levels of chemokines in tumors and in circulation. Interestingly, tumor expression of CXCL8 is negatively correlated with DARC/ACKR1 expression in tumors while circulating levels of CXCL8 are positively correlated with DARC/ACKR1 expression in tumors, a finding that is recapitulated in our survival analyses. This provides an unmasking of a distinction in DARC/ACKR1 control of CXCL8 compared to CCL2 that is likely related to DARC/ACKR1 isoforms.

Previous studies have already shown that the spatial expression of DARC/ACKR1 is governed, at least in part, by the Duffy-null allele (rs2814778). Given that AA cohorts may have over 70% allele frequency of this allele, it can be expected that most AA's would carry the allele and therefore have distinct regulation of the gene in certain tissues. Based on our findings, this allele would predispose breast cancer patients who are Duffy-null carriers to having a specific tumor phenotype, related to the immune response that is directed by the DARC/ACKR1 expression in tumors. Our case-control cohort indicates that the Duffy-null genotypes are a stronger indicator of circulating chemokines, compared to correlations that use self-identified race. The differences in chemokine correlations among race groups, compared to strict heterozygote/homozygote allele groups, corresponds to what would be expected within an admixed population where alleles related to genetic ancestry are convoluted within the proxy of race, where a portion of the individuals that may self-identify with African ancestry are harboring a non-African allele. Therefore, the associations of DARC/ACKR1 and chemokine levels in breast cancer cases can be rationally interpreted as ancestry-associated.

Our discovery of a single genetic marker that could definitively regulate the course of immune response in tumors and therefore could forecast TAL profiles to be an invaluable biomarker to identify patients suitable for immunotherapies. In this disclosure, we have identified such a biomarker, showing that tumor expression of an atypical chemokine receptor, DARC/ACKR1, is associated with immune response. This suggests that DARC/ACKR1 can modulate the chemo-attractants in breast cancer patients, ultimately directing the actions of immune cells within the tumors.

The present disclosure indicates the feasibility of integrating single-marker tumor IHC with a multi-marker peripheral blood assay. In combination, our data has shown that differences in tumor immune cell profiles, that are relevant to race, are associated with the tumor expression of DARC/ACKR1. Specifically, the African-specific Duffy-null variant of DARC/ACKR1, which is already associated with the gene's spatial expression, determines a unique biological scenario for distinct TAL infiltrates. This finding has high relevance in cancer management, as a functional regulator of pro-inflammatory and chemotactic cytokines that can specify an infiltrating tumor immune cell type profile and specify differences between patients of distinct ancestry. This further implicates DARC/ACKR1 in tumor phenotype distinctions that could significantly drive treatment outcomes that lead to cancer mortality disparities.

Our findings indicate that the allele of DARC/ACKR1 modulates cancer-specific, circulating chemokine levels and thereby may regulate the distinct tumor infiltration of distinct immune cell profiles observed in tumors expression DARC/ACKR1 at high vs low levels.

TABLE 7

Case-Control Cohort Characteristics

| Characteristic | Cases, n (%) n = 70 | Controls, n (%) n = 151 |
|---|---|---|
| Age (years) | | |
| Mean (±SD) | 64.89 (±11.73) | 45.60 (±16.31) |
| Median (Range) | 64 (46-90) | 42 (20-79) |
| Ethnicity | | |
| White-American | 47 (67.14) | 108 (71.52) |
| African-American | 23 (32.86) | 43 (28.47) |
| Molecular Subtype | | |
| Lum A | 174 (65.41) | — |
| Lum B | 25 (9.40) | — |
| HER2'0 | 37 (13.91) | — |
| Basal-like | 25 (9.40) | — |
| HR+ | 5 (1.88) | — |
| Clinical Stage | | |
| I | 183 (68.54) | — |
| II | 62 (23.22) | — |
| III | 10 (3.75) | — |

TABLE 7-continued

Case-Control Cohort Characteristics

| Characteristic | Cases, n (%) n = 70 | Controls, n (%) n = 151 |
|---|---|---|
| IV | 5 1.87) | — |
| Other | 5 (1.87) | — |
| Not Available | 2 (0.75) | — |
| DARC/ACKR1 Genotype (rs2814778) | | |
| AA | 45 (69.23) | 107 (78.10) |
| AG | 7 (10.77) | 12 (8.76) |
| GG | 13 (20.00) | 18 (13.14) |
| DARC/ACKR1 RBC Phenotype | | |
| Positive | 31 (67.39) | 40 (88.89) |
| Intermediate | 11 (23.91) | 3 (6.67) |
| Negative | 4 (8.70) | 2 (4.44) |

Lum A, Luminal A; Lum B, Luminal B; HER2+, Human Epidermal Growth factor Receptor; HR, Hormone Receptor; RBC, Red Blood Cell; IHC, Immunohistochemistry Example 2

Figure 13:
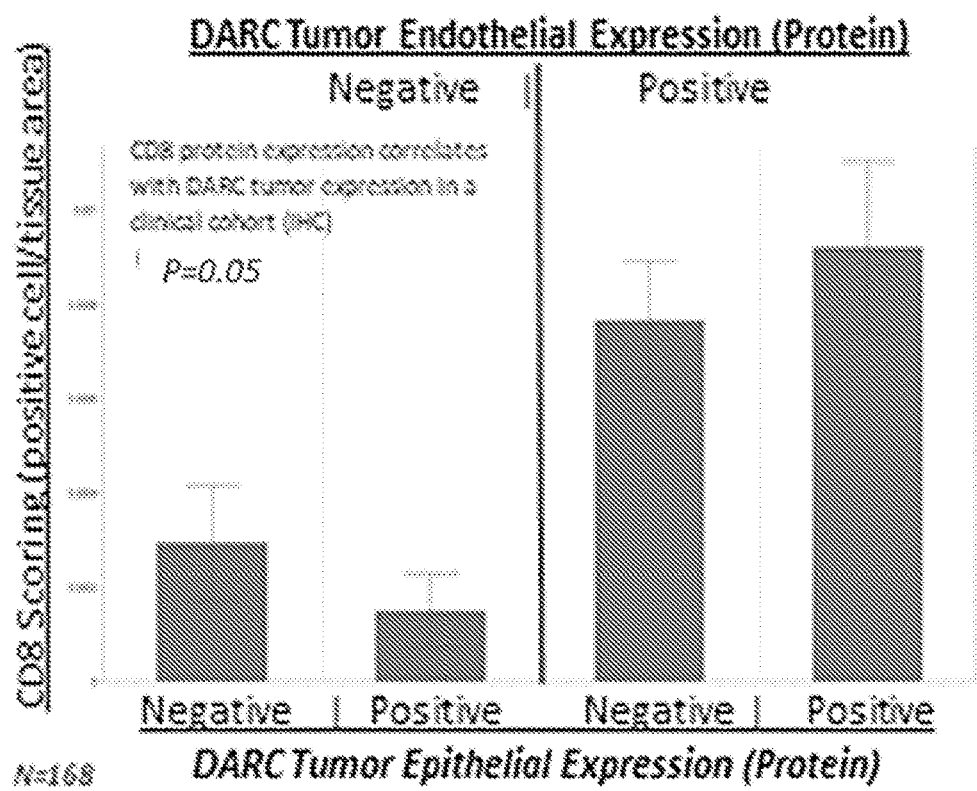
FIG. 13. Supporting clinical data to validate public genomics data. A. Clinical cohort of 168 patients shows significant correlation of DARC tumor status and CD8+ T-cell infiltration as measured by standard clinical IHC procedures. B. Previously identified correlation of CD8+ Tcells and DARC expression by RNAseq computational analyses.
Figure 13:
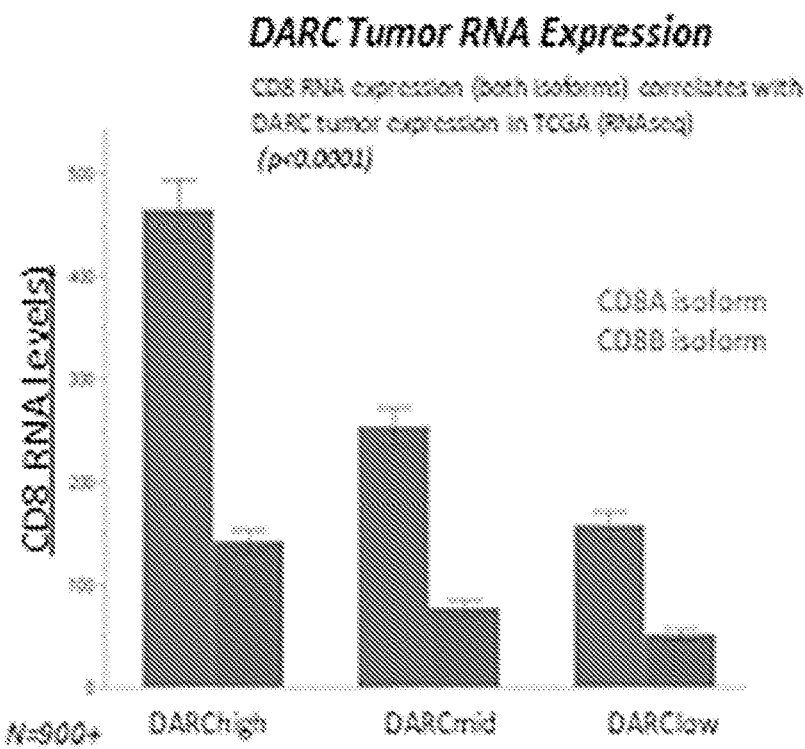

To validate our findings from public datasets, showing that increasing levels of DARC gene expression is associated with increasing counts of tumor infiltrating immune cells, we utilized a clinical cohort of over 200 cases to conduct protein (gene product) investigations. Our data show specific immune cell types that are associated with protein levels of DARC, a validation of computational estimates from RNA sequencing (RNAseq) data. FIG. 13 shows the clinical cohort validation, using ImmunoHisto-Chemistry (IHC) of both DARC status and CD8-positive Tcell scores (Panel A). Panel B, shows the CD8 marker analysis we recently identified from public data sets. Specifically, we show that the CD8 (T-Cell marker) is positively correlated with the DARC expression in both the tumor and endothelial (blood vessels) in the tumor space. In clinical samples, DARC negative tumors (invasive) show very little immune cell infiltration, with a high degree of immune cell activity in the stromal microenvironment; whereas DARC positive tumors (invasive) have a high degree of immune cell infiltration which is associated with endothelial cells (CD31). Using Mass-Cytometry, similar to the IHC scoring data above, CD8 positivity is very high in DARC positive tumors compared to DARC negative tumors. This distinction is also clinically relevant as it outlines the specific mechanism of DARC's control of infiltration, which will be associated with infiltration through the vasculature of the tumor and/or invasion from the interstitial surface of the tumor. Having this distinction of epithelial vs endothelial expression may also aid in tumor cell type discernment as well. In summary, DARC negative tumors possess compoartmentalized immune cells that are isolated to the stroma; the only ki67 (proliferation marker) staining infiltrating the tumor space is associated with tumor cells and CD8+ T cells; and there are some CD8+ T cells around the periphery. DARC positive tumors display infiltration of all immune cells around vessels (CD163, CD3, CD68, and CD8) and also show Ki67 (proliferation) marker staining associated with tumor cells and CD68+ cells.

A possible mechanism of action of DARC's recruitment of T-Cells is through the Helper Tcell pathway, which relies upon the gradient of cytokines that DARC binds and regulates. Specifically, DARC's role may likely not only impact the infiltration of T-Cells, but also the activation of macrophages, and the proliferation and differentiation of B-Cell subtypes as well. The diagnostic use is also verified in the case DARC has specific cytokine affinities, and this single biomarker can correlate with not only the levels of these signaling molecules, but also the downstream impact of immune cell infiltration. Hence a single biomarker test may replace a suite/panel of 10-15 other markers to define the immune-phenotype necessary to make effective treatment decisions involving immunotherapy.

Figure 14:
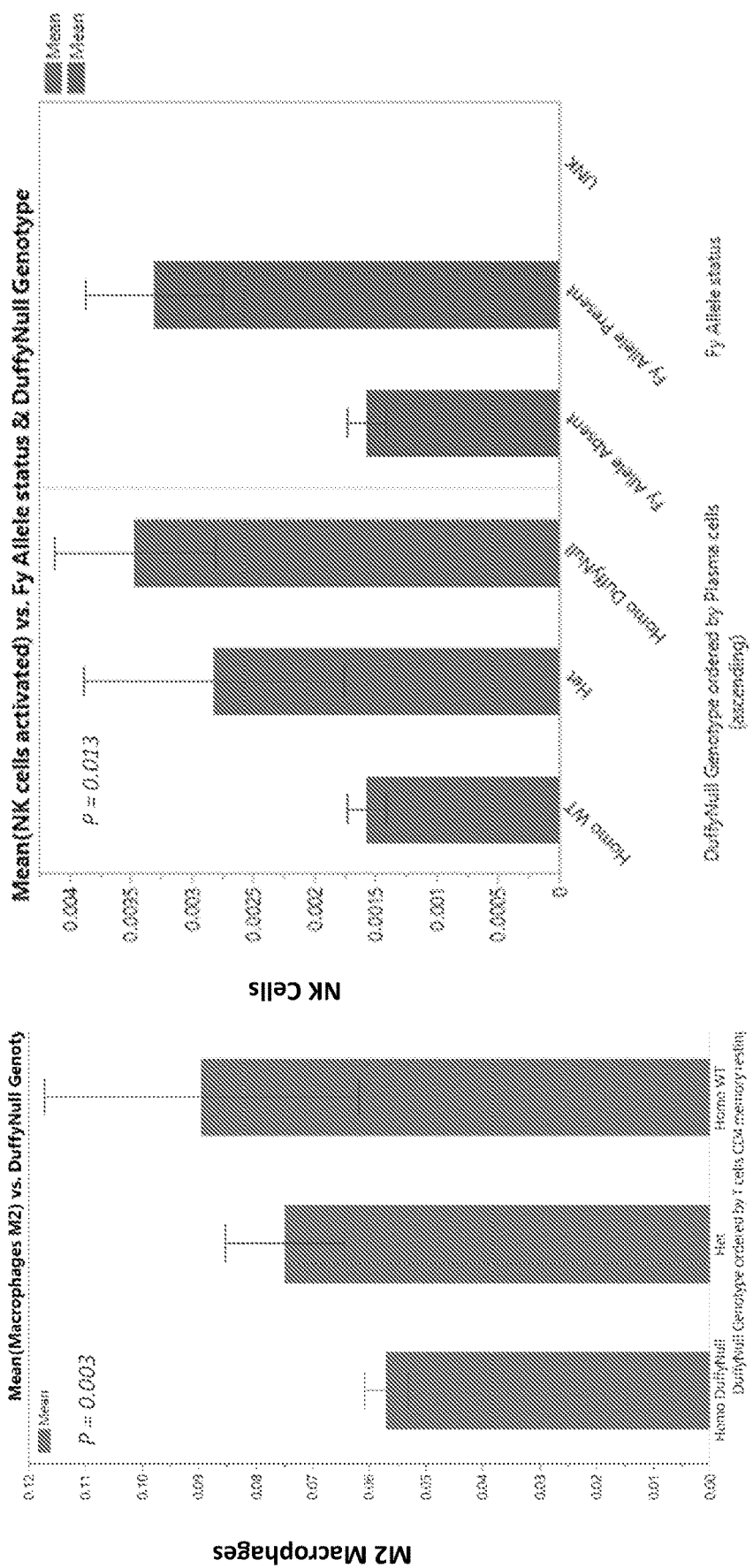
FIG. 14. Duffy-null (DARC mutation) status and immune cell infiltration. Both M2 macrophages (Left) and NK cells (right) show increasing levels of infiltration with higher counts of Duffy allele (i.e. heterozygous=1 allele, homozygous Duffy Null=2 alleles). This mimics the dose-dependent expression of DARC-associated immune cells.

To test the association of the Duffy-null genotype, we also determined the genotype status of the breast cancer cases in the public TCGA dataset. We further determined that the genotype for Duffy-null is also a significant predictor of specific immune cell infiltration, as defined by computational methods (FIG. 14).

Example 3

Breast Cancer Transgene (Tg+) and Ackr1/DARC Knockout Mouse Model.

To generate transgene positive experimental mice with varying levels of ACKR1 expression, the breeding scheme is as follows: Male C3(1)Tag+/0 mice with be bred with Ackr1−/− female mice, to generate the target C3(1)Tag+/0; Ackr1+/− male mouse. This male can be crossed with an Ackr1+/− female, to generate C3(1)Tag+/0 Ackr1+/+, with normal ACKR1 expression, Ackr1+/−, with reduced expression, and Ackr1−/−, with no ACKR1 expression.

sDuffy-Null BMD Breast Cancer Model.

To recapitulate the Duffy-Null phenotype, we have developed the following BMD chimera model: female C3(1) Tag+/0; Ackr1+/−(progeny from the first cross from above) can be lethally irradiated, and serve as BM recipients for Ackr1−/− BM donors. After successful BM transfer, all BM derived cells will be ACKR1 negative, leading to a female mouse that will spontaneously develop breast cancer, that will retain epithelial and endothelial expression of ACKR1, but lack the protein completely on circulating cells.

Experimental Treatment Groups and Monitoring of Tumor Development.

To determine whether DARC expression on epithelial tissue influences the effectiveness of PD-1 inhibitors, target mice of each ACKR1 expressing genotype (homozygous knockout, heterozygous knockout and BMD—blood cell duffy-null) can be taken, and mice of each respective genotype can be divided into one of two treatment arms, PD-1 inhibitor, and placebo treatment. Treatment can be administered when mice are 3 months of age, as the cancer will be invasive at this age, and a dose can be given weekly until the predetermined time-points indicated below. In our BMD chimera model, the BM recipient female mouse can be lethally irradiated at 8 weeks of age, and receive the BM transplant within 24 hours of irradiation. The mouse can be monitored until 3 months of age for tumor progression and any adverse outcomes from the irradiation and BM transfer procedures. Like the above model, at 3 months of age, half of the mice can be assigned to the PD-1 inhibitor arm, where they can receive a weekly dose of PD-1 inhibitor, and the other half will receive placebo treatment. In both of the above models, after treatment administration, mice can be monitored daily for palpable tumors, and aged to predetermined time points of 6, 8 and 12 weeks post treatment. Mice can be culled if palpable tumors exceed 1.5 cm in the greatest dimension, or if they can no longer participate in activities necessary for survival.

To Evaluate Differences in Tumor Growth and Response in the Treatment Versus Placebo Arm, at Designated Time Points, we Will Assay the Following:

Quantify Changes in Circulating Chemokine Profiles to Between PD-1 Inhibitor Treatment and Placebo.

One of the main functions of ACKR1 is to modulate levels of chemokines in circulation through expression on RBC. From previous work, we know that loss of ACKR1 expression in circulation leads to changes in the circulating chemokine profile. Using a multiplex Luminex assay on plasma collected at tissue harvest, we can additionally determine how both varying expression of ACKR1 and the PD-1 inhibitor treatment will alter the circulating chemokine profile.

Visualize Co-Localization Patterns of ACKR1, Target Chemokines, and Infiltrating Leukocytes Between PD-1 Inhibitor and Placebo Groups Among Ackr1++; Ackr1+− and Ackr1−/− Breast Cancer Transgenic Mice Using Immunofluorescent Staining Techniques on Fixed, Paraffin-Embedded Mammary Tumors.

At tissue harvest, distinct tumors can be dissected, in addition to the upper and lower mammary glands of the mice. These can be fixed, and paraffin-embedded, and standard immunofluorescent staining procedures can be followed to visualize patterns of expression of ACKR1, target chemokine ligands, and infiltrating leukocytes. From leukocyte staining, we can also determine the degree at which leukocytes infiltrate versus encapsulate the cancerous duct, and if these patterns of recruitment and infiltration change based on differences in ACKR1 expression, and PD-1 inhibitor treatment.

Quantify Profiles of Target Chemokines and Infiltrating Leukocytes Between PD-1 Inhibitor and Placebo Groups Among Ackr1+/+; Ackr1+/− and Ackr1−/− Breast Cancer Transgenic Mice Through Multiplex Luminex Assays and Flow Cytometry Methods on Tumor Protein Dissociations.

To quantify chemokine and leukocyte invasion in the TME, tumor dissociation procedures can be utilized followed by multiplex Luminex assay, to determine any changes in the chemokine profiles, and flow cytometry methods, to determine differences in the immune cell profile of the TME between our different ACKR1 expressing and treatment groups.

Expected Outcomes.

Based on the present disclosure, we predict in our models that Ackr1+/+ mice that receive PD-1 inhibitor will have attenuated or reduced tumor growth—As functioning ACKR1 protein will modulate chemokine levels to recruit back infiltrating leukocytes, infiltrating T cells will become activated, and subsequent T cell mediated tumor cell killing will take place as PD-1 will be unable to bind upregulated PD-L1, and the tumor cells will be unable to escape the T cell response. Ackr1−/− mice that receive treatment should have less tumor growth than those null mice that received placebo, but reduced ACKR1 expression will lead to decreased immune cell infiltrate, including T cells. This means that the tumor response to PD-1 inhibitor will be attenuated.

Discussion

Through TCGA gene expression data analysis, we have recently shown that DARC expression is positively and significantly correlated with abundance of tumor-associated leukocytes in the TME. Within breast cancer cases, you can find a broad distribution of leukocyte infiltration, but the molecular subtype most commonly found to have more of this infiltration are triple-negative breast tumors (Beckers et al., Histopathology, 2016. 69(1): p. 25-34, Disis et al., Breast, 2018. 37: p. 196-199). This is an interesting paradox, as in breast cancer, higher levels of leukocyte infiltration are correlated with better prognostic outcomes (Beckers et al., Histopathology, 2016. 69(1): p. 25-34), however the molecular subtype where we observe the most infiltration is associated with the worst prognosis compared to other molecular subtypes of the disease.

Alongside increases in leukocyte infiltration, we also see an upregulation of PD-L1 expression on tumor cells (Beckers et al., Histopathology, 2016. 69(1): p. 25-34), driven by release of pro-inflammatory cytokines by TCR/MHC binding between T cells and tumor cells (Buchbinder et al., Am J Clin Oncol, 2016. 39(1): p. 98-106). This cascade weakens T cell mediated tumor cell killing, as PD-1 on T cells is binding the upregulated PD-L1 present on tumor cells. Another consequence of pro-inflammatory cytokine release is the secretion of inflammatory chemokines (Arango Duque et al., Front Immunol, 2014. 5: p. 491). ACKR1 plays a key role in modulating levels and helping to establish gradients of these chemokines (Nibbs et al., Nat Rev Immunol, 2013. 13(11): p. 815-29), which in turn are recruiting more leukocytes back to the TME. As PD-1 and PD-L1 are continually up-regulated, these T cells are being recruited into the environment, but rendered ineffective as the action of the T cells is now inhibited by PD-1/PD-L1 binding. In a DARC expressing TME, if PD-1 and PD-L1 binding were inhibited by PD-1 inhibitors, T cells would be able to resume their T cell mediated tumor cell killing, and continual release of inflammatory chemokines would help insure that leukocytes continue to infiltrate the TME, and specifically that T cell can be activated and participate in tumor cell killing.

Figure 15:
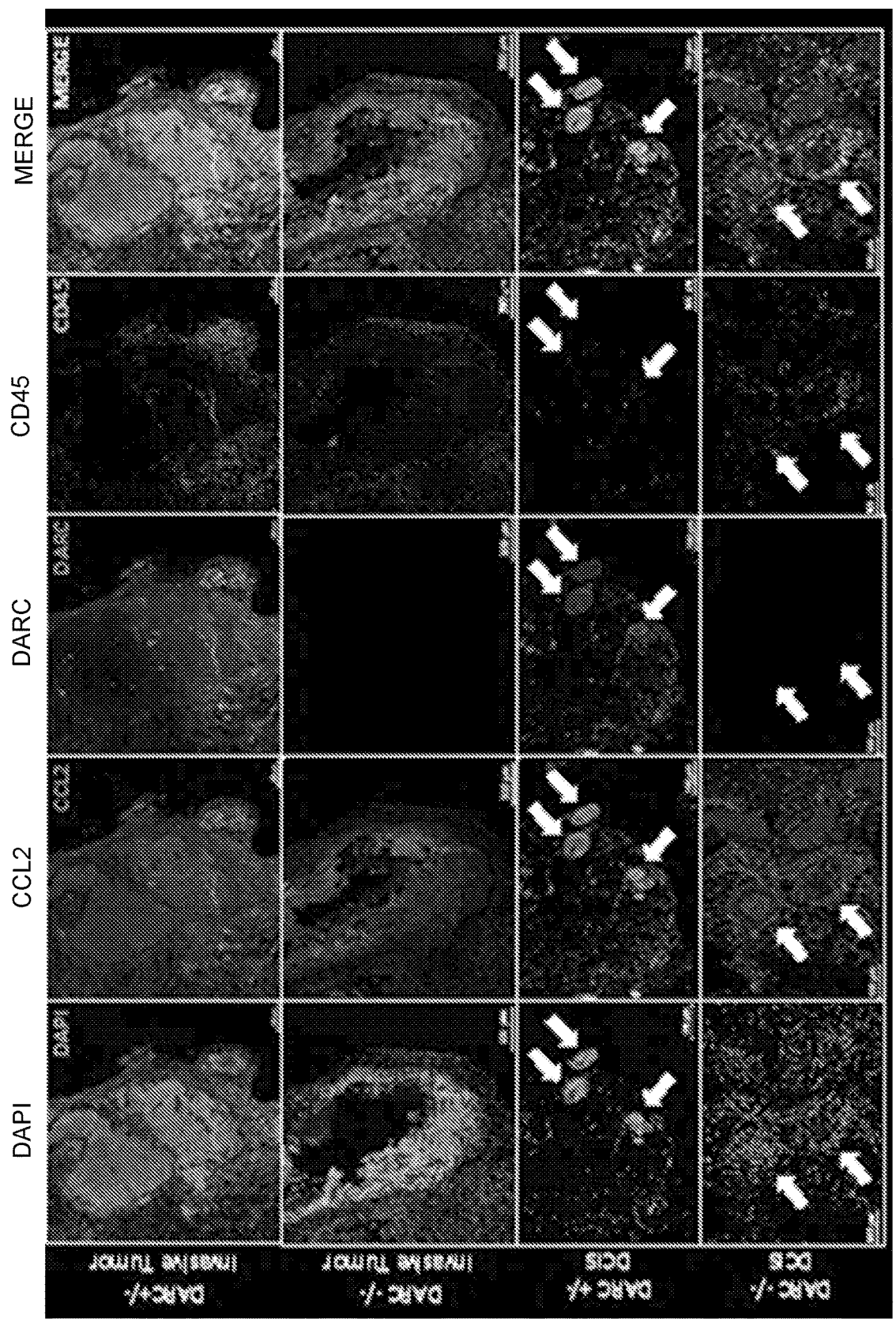
FIG. 15. Mouse model characterizations of DARC-positive vs DARC-negative tumors for the indicated staining.

DARC modulates the levels of inflammatory chemokines and helps establish gradients for effective leukocyte recruitment through expression by trancytosing chemokines when expressed in tissues, and acting as a chemokine sink when expressed on red blood cells. We show that DARC is expressed on tumor epithelial cells in the breast, where it can modulate inflammatory chemokine levels and therefore leukocyte recruitment into the tumor microenvironment. Similar to the findings in human tumors, mouse tumors that are DARC negative have immune cell (CD45 marker) sequestration around the edges of the tumor, with little, to no, infiltration. (FIG. 15).

CAR-T Cell Treatment

Because DARC drives the infiltration of antigen presenting cells, based on the present disclosure, we anticipate that tumors with DARC expression would have a higher immunogenicity than those that do not express DARC. Specifically, in our mouse model, we dissociate tumors and isolate T-cells to expand in vitro. We also compare the ability of these T-Cells to interact with cultured organoid tumor cells in an effort to quantify the immune response action. We can determine that tumors that have DARC expression also have T cells which have a high-response (progressive immune response). We can determine that DARC negative tumors have a low-response T-cell population (if any T cell infiltration at all).

Although the present disclosure has been described with respect to one or more particular embodiments and/or examples, it will be understood that other embodiments and/or examples of the present disclosure may be made without departing from the scope of the present disclosure.

What is claimed is:

1. A method of treating an individual afflicted with breast cancer with an immunotherapy comprising:
   i) testing for the presence or absence of Duffy-null mutation comprising a T to C substitution in rs2814778 in the genome of breast cancer cells obtained from the individual;
   ii) determining the Duffy-null mutation is not present on one or both alleles to thereby identify the individual as suitable for immunotherapy; and
   iii) treating the individual identified as suitable for the immunotherapy with an immune checkpoint inhibitor.

2. The method of claim 1, wherein the immune checkpoint inhibitor comprises an antibody that targets PD-1, PD-L1, CTLA-4, LAG3, B7-H3, B7-H4, or TIM3.

3. The method of claim 2, wherein the antibody that targets PD-1 is nivolumab or pembrolizumab.

4. The method of claim 2, wherein the antibody that targets PD-L1 is BMS-936559 or MPDL3280A.

5. The method of claim 2, wherein the antibody that targets CTLA-4 is ipilimumab or tremelimumab.

* * * * *

SEQUENCE LISTING

<160> NUMBER OF SEQ ID NOS: 6

<210> SEQ ID NO 1
<211> LENGTH: 30
<212> TYPE: DNA
<213> ORGANISM: Homo sapiens

<400> SEQUENCE: 1
tccttggctc ttatcttgga agcacaggcg        30

<210> SEQ ID NO 2
<211> LENGTH: 30
<212> TYPE: DNA
<213> ORGANISM: Homo sapiens

<400> SEQUENCE: 2
cgcctgtgct tccaagataa gagccaagga        30

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
tctgggtatg tcctccaggc        20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
aagggcagtg cagagtcatc        20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
tccaatttcc cagcacctcc        20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
ggctggttgg gactacactc        20